United States Patent
Kumakhov

(10) Patent No.: US 6,963,072 B2
(45) Date of Patent: Nov. 8, 2005

(54) INTEGRAL LENS FOR HIGH ENERGY PARTICLE FLOW, METHOD FOR PRODUCING SUCH LENSES AND USE THEREOF IN ANALYSIS DEVICES AND DEVICES FOR RADIATION THERAPY AND LITHOGRAPHY

(76) Inventor: Muradin Abubekirovich Kumakhov, Russia, 123298, Moscow, ul. Narodnogo Opicheniya, d. 35, kv. 55, Moscow (RU) 123298

( * ) Notice: Subject to any disclaimer, the term of this patent is extended or adjusted under 35 U.S.C. 154(b) by 12 days.

(21) Appl. No.: 10/458,649

(22) Filed: Jun. 11, 2003

(65) Prior Publication Data

US 2003/0209677 A1   Nov. 13, 2003

Related U.S. Application Data

(62) Division of application No. 09/868,189, filed as application No. PCT/RU00/00206 on May 30, 2000, now Pat. No. 6,678,348.

(30) Foreign Application Priority Data

Oct. 18, 1999  (RU) .................................. 99121677

(51) Int. Cl.⁷ ............................................. G02B 5/124
(52) U.S. Cl. ..................... 250/505.1; 378/85; 378/149
(58) Field of Search ..................... 250/505.1; 378/84, 378/85, 149

(56) References Cited

U.S. PATENT DOCUMENTS

| | | | |
|---|---|---|---|
| 5,001,737 A | | 3/1991 | Lewis et al. |
| 5,192,869 A | * | 3/1993 | Kumakhov ............... 250/505.1 |
| 5,276,724 A | | 1/1994 | Kumasaka et al. |
| 5,570,408 A | * | 10/1996 | Gibson ....................... 378/145 |
| 5,744,813 A | * | 4/1998 | Kumakhov ............... 250/505.1 |
| 5,745,547 A | | 4/1998 | Xiao |
| 5,812,631 A | * | 9/1998 | Yan et al. ..................... 378/85 |

FOREIGN PATENT DOCUMENTS

| | | |
|---|---|---|
| EP | 0 824 026 A2 | 2/1998 |
| WO | WO092/08235 | 5/1993 |

* cited by examiner

Primary Examiner—John R. Lee
Assistant Examiner—Paul M. Gurzo
(74) Attorney, Agent, or Firm—McGuireWoods LLP

(57) ABSTRACT

The invention makes possible to increase the degree of radiation focusing by the lens, to use particles of higher energies, and to increase the coefficients, depending on these factors, of the devices, the lens is used in. Thus the sublens 18 of the least degree of integration represents a package of the channels 5, which is growing out of joint drawing and forming the capillaries, which are laid in a bundle. The sublens of each higher degree of integration represents a package of sublenses of the previous degree of integration, which is growing out of their joint drawing and forming. The sublenses are growing out of performing the said operations at the pressure of the gaseous medium inside the channels being higher than the pressure in the space between the sublenses of the previous degree of integration and at the temperature of their material softening and splicing the walls. To produce the lenses a bundle of stocks (capillaries) in a tubular envelope is fed to the furnace (at the first stage) or stocks, produced on the previous degree, and the bundle is drawing from the furnace at the speed, exceeding the speed of feeding. The product is cut off on stocks for the next stage, and at the final stage the product is formed by varying the drawing speed, after what the parts with formed barrel-shaped thickenings are cut of.

12 Claims, 16 Drawing Sheets

INTEGRAL LENS FOR HIGH ENERGY PARTICLE FLOW, METHOD FOR PRODUCING SUCH LENSES AND USE THEREOF IN ANALYSIS DEVICES AND DEVICES FOR RADIATION THERAPY AND LITHOGRAPHY

CROSS REFERENCE TO RELATED APPLICATIONS

The present application is a divisional application of U.S. application Ser. No. 09/868,189 filed on Jun. 15, 2001 Pat. No. 6,678,348, all of which is incorporated by reference in its entirety herein.

BACKGROUND OF THE INVENTION

1. Field of the Invention

The present invention generally relates to radiation lenses and, more particularly, to x-ray lenses comprising a plurality of sub-lenses drawn together which is useful in flaw detection and diagnostics in engineering and medicine.

2. Description of the Prior Art

The usage of different types of radiation (X-rays, gamma ray, neutral or charged particle radiation) in different fields, such as instrument making, medicine, microelectronics, etc., considerably broadened for the last 20–30 years. More powerful X-ray and safe neutron sources are made. These sources help to solve important fundamental and applied tasks of science and industry.

Unfortunately, x-ray sources are very expensive. To build such sources, as does the European Center for Synchrotron Radiation (Grenoble, France), several states must cooperate. Therefore it is very important to create optical devices, which can significantly increase effective luminance of cheap and available sources.

In the late eighties—early nineties of 20 century the lenses for controlling X-rays and other high-energy radiation were created.

The first lenses for radiation control (including divergent radiation focusing, parallel beam of divergent radiation, a parallel radiation focusing or other transformation) comprised a package of channels for radiation transportation, and in these channels the radiation experiences multiple total external reflections. Such lenses were made of mass of capillaries or polycapillaries, which pass through holes or cells of supporting systems, positioned on definite distances along the lens such as disclosed in U.S. Pat. No. 5,192,869. A lens is shaped like a barrel (i.e. it narrows down to both ends), if it is meant for a divergent radiation focusing; or a lens is shaped like a half-barrel (i.e. it narrows down to one end), if it is meant for transforming a divergent radiation to quasi-parallel radiation focusing. Later on the terms "full lens" and "half lens", respectfully, became widespread to denote lenses of these two types.

Other forms of lenses are possible, different from "classical" barrel and half-barrel forms, for example, the lens is bottle shaped as the curved body with a geneatrix, having a knee, when the channels are parallel in one or two ends. Such lenses can be used as a radiation filter (for cutting the high-energy part of the source spectrum) for transforming a section size of an input beam, etc.

The lenses described above, relating to the lenses of the first generation, are handmade and very massive. Such lenses focus X-rays with a quantum energy up to 10 keV, and the focal spot is of order of 0.5 mm in diameter.

A monolithic lens is also known, in which the walls of neighboring channels contact each other along their full length and the channels themselves have variable along a length cross-section as disclosed for example in U.S. Pat. No. 5,570,408.

By means of these lenses it is possible to focus a radiation with a quantum energy up to 20–25 keV. A cross-section of a transportation channel is about 10 $\mu$m, and sometimes it is possible to obtain the channels of up to 2–3 $\mu$m size. The minimum size of a focal spot is of the same order. Nowadays these lenses, called lenses of the second generation, are the most effective X-ray concentrators, when using X-ray tubes as the sources. A weakness of monolithic lenses is that it is practically impossible to create lenses with sufficiently big diameter (2–3 cm and more) with submicron channels.

In international publications WO 96/01991 and WO 96/02058 a full lens and a half-lens are described, which are made as a package of micro-lenses, packed very close, each of these lenses is a monolithic lens. Such construction makes possible to obtain accordingly larger cross sizes than in a common monolithic lens. When an aperture increases, an acceptance angle of radiation of a point source increases as well. However, the cross section sizes of channels for radiation transportation and the sizes of the focal spot remain the same, as in a common monolithic lens, and the packing of micro-lenses for needed shaping of the lens must be hand-made.

The technical result, achievable with the suggested lens, implies that the degree of radiation focusing increases owing to decreasing of cross section of the channels, making possible to use the particles of higher energy, as well as simplifying the technology of producing owing to eliminating the necessity of individual adjustment of micro lenses, when packing them in a unified structure.

The suggested method has an analogue; it is the method according to U.S. Pat. No. 5,812,631. According to this method several (two or more) stages of drawing of stocks is realized (the stocks represent a package of stocks in a common envelope, obtained at the previous stage). The regime of drawing the product, which is starting material for producing a lens by cutting the section of this product, from the furnace makes possible in this method to produce a microlens at once. To produce a full lens the product must be drawn repeatedly from the furnace, and this product must be fed in the furnace by the other end. It complicates the technological process.

However, the other defect of this method is more important. It does not provide the pressure correlation, mentioned above, in capillaries and space between stocks. If this condition is not met thin-walled capillaries, which are usually used for producing lenses for the examined purpose, are compressed in the process of drawing (i.e. it is impossible to produce the lens suitable for use). Thus the method according to the U.S. Pat. No. 5,812,631 can be realized (i.e. it allows producing fundamentally efficient lenses) only with the use of capillaries, produced of thick-walled tubes (i.e. a channel diameter of such tube must be comparable with a wall thickness). The same proportion lasts in a ready lens; because of this it has low transparency. For example, if a diameter of a channel is approximately equal to a wall thickness, a transparency lowers by an order. It lowers additionally, because this known method provides producing only such lenses, in which inner envelopes are present, as this method does not include the operation of envelopes removing from the stock surface.

Analytical devices are among one of the applications of X-ray lenses. These devices are meant for structure analysis (density distribution) of objects (including medicine and other biological objects), and for analysis of elemental composition of products and materials. The use of radiation for these aims, namely X-rays, is known for a long time.

A quality new stage in progress of such devices began with the use of lenses for controlling radiation, used in such devices such as described in U.S. Pat. No. 5,497,008. This analytical device includes a radiation source, representing a neutral or charged particle radiation, and a means for positioning the object under study. This means is positioned so that it is possible to act on it by radiation of the source. Beside that the analytical device includes one or more radiation detectors (the detectors are positioned so that it is possible to act on them by radiation, passed through the object under study or excited in it), one or more lenses for transforming a radiation, representing a neutral or charged particle flux, and being positioned on the radiation path from the source to the object under study and/or on the path from the object under study to one or more said radiation detectors (the detectors include radiation transporting channels, adjoining by the walls, with total external reflection).

Thus known analytical device under U.S. Pat. No. 5,497,008 does not provide high energy, and also cannot create small focal spots, what limits an accuracy and resolution of the analysis.

A technical effect, achievable in the suggested analytical device, is the increase of precision and resolution of the analysis, and also the expansion of opportunities of the analysis at the expense of application of radiation with higher energies, that becomes possible due to advantages of an offered integral lens.

The devices for radiation therapy, including one or more radiation sources, representing neutral or charged particle flux (namely, X-rays, proton flux), an optical system for beam collimation of every source, and a device for positioning the patient's body or its part to be irradiated, are known. When such a device, healthy tissues, being on a radiation path to a tumor, located deep, are irradiated intensively.

The suggested invention, relating to the device of radiation therapy, is aimed at obtaining the following technical result: a doze of irradiation, acting on the tissues around the tumor, decreases.

One more field of application of X-ray lenses is microelectronics, namely X-ray lithography.

The device is known for contact X-ray lithography, containing a source of soft X-rays, a lens for transforming a divergent radiation to quasi-parallel, including radiation transporting channels, adjoining by their walls, with total external reflection, and the means for placing a mask and substrate with the resist put on it (see, U.S. Pat. No. 5,175,755).

In this patent the lenses of the first and second generation are suggested for usage in the lithography. However, any of these types of lenses does not provide the solving a problem of lithography in microelectronics. In assembled lenses (lenses of the first generation), in monolithic lenses (lenses of the second generation) the size of the channel on an input about 1 μm and on an output about 0.1 μm is technologically impossible to implement at the target aperture 10 cm$^2$ and more, what is necessary for lithography in the microelectronics.

The technical result of the suggested invention, related to the device for contact lithography, is obtaining a means, suitable for use in the microelectronics.

It is also known from U.S. Pat. No. 5,175,755 a device for projection X-ray lithography. This device includes a source of soft X-rays, a lens for transforming a divergent radiation of the source to quasi-parallel, meant for the irradiation of the mask, a device for the mask positioning, a lens for X-ray image of the mask transmission with the decrease of its size to the resist, a means for placing the substrate with the resist put on it. In this case both said lenses include the radiation transporting channels, adjoining by their walls, with total external reflection.

This device, at use in it the lenses of the first and second generations (i.e. assembled and monolithic lenses), known at the moment, as well as the device for contact lithography, discussed above, are unsuitable for use in microelectronics in view of impossibility to gain in such lenses diameters of channels, providing required accuracy of presentation of the mask image on the resist.

The technical result of the invention, related to the device for the projection lithography, is the production of the device, suitable for use in the microelectronics.

SUMMARY OF THE INVENTION

The present invention is directed to a radiation lens made up of a plurality of sub-lenes. In particular, a bundle of capillaries capable of guiding x-rays or similar neutral or charged radiation are drawn (pulled) together in a gaseous atmosphere at a heat sufficient to soften and bond the capillaries to form a unified sub-lens. The pressure of the gas atmosphere outside of the capillaries is made less than the pressure inside the capillaries to prevent the capillaries from collapsing. Thereafter, a bundle of sub-lenses are similarly drawn together in the gaseous atmosphere and at a heat sufficient to soften and bond the sub-lenses together to form higher integration sub-lenses. This process is repeated, each time drawing together the previous integration level sub-lenses to form higher integration level lenses until a single unified lens is formed of the desired size. The ends of the capillaries are cut to form an input face of the lens and an output face of the lens. Capillaries at the input and/or output faces can be oriented toward a focal point for divergent radiation applications or oriented in parallel for quasi-parallel radiation applications.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
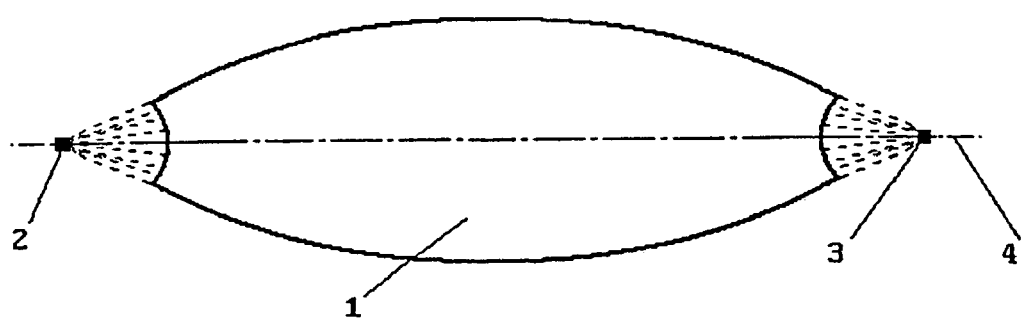
FIGS. 1, 8, and 9 depict the schematic pictures of a full lens, a half-lens and a lens, made as an axis-symmetric body with the geneatrix, having a knee, respectively.

To gain the technical result, mentioned above, proper in the suggested lens for radiation transforming, representing the neutral or charged particle flux, this lens contains the radiation transporting channels, adjoining by the walls, with total external reflection, oriented by input ends so that to capture a radiation of the source in use.

Unlike known lenses, the lens according to the present invention is made as a package of sublenses of various degree of integration. As this takes place, a sublens of the least degree of integration represents a package of radiation transporting channels, which is growing out of the joint drawing and forming of capillaries, packed in the beam, at the pressure of gaseous medium in the space between them less than the pressure inside channels of capillaries, and the temperature of softening of the material and splicing the walls of the adjoining capillaries. A sublens of every higher degree of integration represents a package of sublenses of the previous degree of integration, growing out of their joint drawing and forming at the pressure of the gaseous medium in the space between them less than the pressure inside the channels of sublenses, and the temperature of softening of the material and splicing the adjoining sublenses. The ends of this unified structure are cut and form an input and output ends of the lens.

The unified structure and the lenses of each degree of integration can have an envelope, made of the same material, as capillaries, or very close to it on value of the coefficient of thermal expansion.

The envelopes increase the rigidity of the structure and the lens strength. However, a lens, in which the sublenses do not have envelopes, is more transparent.

The inventive lens is named an integral lens because of combination a great amount radiation transporting channels ($10^6$ and more) in it (therefore with reference to sublenses the concept of a degree of integration is used), has channels with smaller cross-section, than the prior art monolithic lens, or miniature lenses, as the channels diameter diminishes on the every stage of drawing. Correspondingly the degree of radiation focusing increases, i.e. a size of the focal spot decreases.

All sublenses of the highest degree of integration can be packed in a common envelope. The latter in this case is an external envelope of a lens.

In some applications a presence of coating of one or more layers, made of one and the same or different chemical elements, on the inner side of walls of the channels is useful. Before producing an integral lens the coatings are applied on the inner side of a tube, the capillaries are resulting from. Thus it is important, that the coefficient of heat expansion of the material, coatings are made of, should be close to the coefficient of heat expansion of the material, the capillaries are produced from. In this case the process proceeds without complications. Multilayer periodical coatings allow to implement advantages, caused by interference phenomena, incipient at reflection from the surfaces, having such coatings. In particular, radiation monochromation, transported through the channels with the walls, having such coatings, is possible. The application of rough coating gives an appearance of diffusion component at reflection and can develops the conditions for radiation transporting at the angle of incidence, exceeding the critical angle of the total external reflection.

The full integral lens, as well as known lenses of the previous generations, is made with a capability of a divergent radiation focusing; for this purpose input and output ends of the radiation transporting channels are oriented, accordingly, to the first and second focal points. In first of them the radiation source is placed, when using the lens; in the second point the focal spot of the lens is forming.

An integral half-lens is used for transforming the divergent radiation to quasi-parallel, as well as at use of lenses of previous generations. In an integral half-lens some ends are oriented to the first focal spot, and other ends are parallel to each other.

It is not always appropriate to make full integral lenses for the divergent radiation focusing symmetrical. If a size of an X-ray source is large enough, it is worthwhile to make the focal distance from the input end of the lens large, and the focal distance from the output end of the lens lesser in order to obtain small focal spot. For this purpose the radius of curvature of channels of a half of lens, adjoining to an input end, must be larger, than the radius of curvature of channels of a half of lens, adjoining to the output end, i.e. the lens must be asymmetrical with respect to the cross-section medial on its length.

An integral lens can be made as an axi-symmetric body, as well, with the generatrix, having a knee, and different diameters on the part of an input and output, in particular for changing the size of cross section of the transported beam. In this case the lens is "bottle" shaped.

It is a traditional demand in the process of creating lenses: all transporting channels of lenses must be filled with radiation completely. For this purpose it is necessary that the filling factor $\gamma = R(\theta c)^2/2d$ was more or equal to 1 (here R is the radius of curvature of the channel, d is the diameter of the channel, $\theta c$ is the critical angle of total external reflection).

However, the executing of this requirement is not always appropriate. In a case, when $\gamma \geq 1$, the size of the focal spot of the lens is equal to $d + 2f_{output}\theta c$, where $f_{output}$ is the size of the focal spot of the lens on the part of an output. It means that it is impossible to make the size of the focal spot of the lens less than d. If $\gamma \geq 1$ fails, that will take place only partial filling of the channels with a radiation. Thus X-ray photons or neutrons "force" against the side of walls of transporting channels, peripheral with respect to an optical axis of the lens. If the factor γ<<1 takes place, the effective size of the channels can be much less, than the size of channels d. Thus the total transmission of the lens decreases. But the size of the focal spot decreases proportionally also, and the area of the focal spot decreases even more sharply, due to what radiation density in the focal spot grows.

Lenses of viewed purpose have aberrations, consisting that the position of the focal spot in lengthwise direction is rather spread. The characteristic size of spreading, as a rule, exceeds in tens and more times the size of the focal spot in the crosswise direction. The radiation transporting channels, adjoining to the optical axis of the lens, give the very major contribution to the spreading. The participation of these channels in the forming of the focal spot gives as well a magnification of the crosswise sizes of the spot, as these channels have less curvature (down to zero), and it is impossible to execute the requirement γ<<1, and even γ<1 for them.

In one of special cases of embodiment of the suggested lens it is possible to except the influence of these channels on the spreading of the focal spot in lengthwise direction and magnification of its crosswise sizes by closing the part of lens, adjoining to the optical axis, on the part of the input or output by screens, or by making this part impermeable for the radiation by the other method. For example, it would be possible to make continuous (without channels) that part of the lens, where sublenses could be, and for their channels γ≧1.

The specific of the other special cases of embodiment of the suggested lens is that the channels of one or more sublenses, placed near the lengthwise axis of the lens, are made with a capability of radiation transporting at a single total external reflection or without it. For this purpose they can be made, for example, of smaller length, than the channels of sublenses, which are more distanced from the lengthwise axis of the lens. Owing to this fact, losses of a radiation in the channels of the sublenses reduce, and the overall transmission coefficient of the lens increases. The same result is obtained (but in combination with the increase of spreading of the focal spot) when the central channels are made of a major diameter.

The operations, being carried out on the different stages of the technological process of producing of the suggested integral lens, are of the same tape and do not depend on the degree of integration of the sublenses, used at every stage. The most suitable material for producing integral lenses is glass; it is possible to use other materials, for example, ceramics, metals, alloys.

The suggested method of producing the integral lenses, includes two or more stages of embodiment of stocks, placed in a tubular envelope. Thus the capillaries are used at the first stage as stocks, and at every next stage the stocks, which are growing out of the realization of the previous stage, are used.

As against the previous one, in the suggested method the tubular envelope with the stocks, filling it, is drawn in the furnace. Thus the feed speed must be kept lower, than the product withdrawal speed, at the constant relation between these speeds. After that the stocks, resulting from this stage, are gained by cutting lengthwise the product, emerging from the oven.

After completion of the last stage, the tubular envelope is filled with the stocks, which are growing out of this stage. Then the tubular envelope with the stocks, filling it, is drawn in the furnace, keeping the feed speed in the furnace lower, than the product withdrawal speed from the furnace, changing periodically the relation between these two speeds to form barrel-shaped thickenings on the finite product. Then the lenses, in the form of parts of the product, are made by cutting lengthwise the finite product. Each lens has only one barrel-shaped thickening.

At all stages of realization of the method the tubular envelopes are used. These envelopes are made of the same material as the capillaries, or very close to this material on the thermal expansion coefficient. The process of drawing of tubular envelopes with stocks, filling the envelopes, is realized at the pressure of the gaseous medium in the space between the stocks less than the pressure inside the channels of the stocks, and the temperature of softening of the material and splicing the walls of the neighboring channels.

In dependence of how the cutting is made (in sections disposed symmetrically or asymmetrically on each end of a maximum of the barrel-shaped thickenings, or in section relevant to a maximum of thickening and on each end of it), symmetrical or asymmetrical full or half-lenses are made.

The regime of drawing speed (relation between the feed speed of the tubular envelope with the stocks in the furnace and the product withdrawal speed from the furnace) defines the lens form. In particular, when this relation (in the process of barrel-shaped thickening forming) changes, the lens with various curvature radius of the channels on different sides of the maximum of barrel-shaped thickening is produced.

The lens as an axi-symmetric body with generatrix, having a knee, and the ends of the channels, being parallel to the lengthwise axis of the lens (a "bottle" shaped lens) is produced by cutting the part of the product, outgoing from the furnace. This part of the product is enclosed between the maximum of the barrel-shaped swelling and the cross-section, being on the other side of the inflection point of the generatrix on the part of the product, where its diameter is constant.

To produce lenses without envelopes, which cover sublenses, each stage of producing the stocks should be finished with etching the envelopes. Similarly, if it is necessary to produce lenses without external envelope, it should be etched.

The suggested analytical device, as well as the known one, more close to it, includes a radiation source (representing neutral or charged particle beam), a means for positioning the subject under study (the means is placed with a capability of a radiation of the source acting on the subject under study), one or more radiation detectors (placed with a capability of a radiation passed through the object under study or excited in it acts on the detectors), one or more lenses for transforming a radiation of the source or radiation, excited in the object under study. These lenses are placed on the radiation way from the source to the object under study and/or on the way from the last one to one or more said radiation detectors. These detectors contain the radiation transporting channels, adjoining by their walls, with total external reflection, and the channels are oriented with their input ends so as to capture the radiation, being transported.

As against known, at least one of the lenses is made as a package of sublenses of a various degree of integration. Thus the sublens of the least degree of integration represents a package of radiation transporting channels, which is growing out of joint drawing and forming the capillaries bundle at the pressure of the gaseous medium in the space between the capillaries, being less than pressure inside the channels of capillaries, and at the temperature of a softening of the material and splicing the walls of the neighboring capillaries. The sublens of each higher degree of integration represents a package of sublenses of the previous degree of integration, which is growing out of their joint drawing and forming at the pressure of the gaseous medium in the space between the sublenses, being less than pressure inside the channels of sublenses, and at the temperature of a softening of the material and splicing the walls of neighboring sublenses. All sublenses of the highest degree of integration are combined in a unified structure, which is growing out of their joint drawing and forming at the pressure of the gaseous medium in the space between the sublenses; being less than the pressure inside the channels of sublenses, and at the temperature of a softening of the material and splicing the neighboring sublenses. The ends of the unified structure are cut, and they form the input and output ends of the lens.

A lot of characteristic geometries of the integral lenses placing in the analytical device together with some other constructive peculiarities of the device.

So, an analytical device can be made with a capability of scanning the surface or volume of the object under study by means of the aligned focuses of the lenses, placed on the way from the source to the object under study and from the last one to the detector. At such geometry three-dimensional local analysis can take place, if the object is scanned in three dimensions. The sensitivity of the method is high enough, as the detector receives the radiation significantly from the area, where both lenses have common focus.

In this geometry a specific case can take place, when an integral lens, placed on the radiation way from the object under study to the detector, forms a quasi-parallel beam, and between the lens and the detector a crystal-monochromator or multilayer diffraction structure are placed with a capability of varying their placement and the angle of incidence of the quasi-parallel beam on them to fulfill the Bragg condition for different lengths of radiation waves, excited in the object under study. The usage of the lens significantly decreases the losses in comparison with the collimation method of producing of a parallel beam, falling on the monochromator.

In the other geometry synchrotron or other source is used as the source, forming a parallel beam, and a lens, placed on the radiation way from the source to the object under study, is made with a capability of such beam focusing.

One more geometry is characterized by the fact, that a source of a broadband X-rays is used in an analytical device. The X-rays is transported simultaneously by two lenses, made with a capability of forming a quasi-parallel beam. Two crystal-monochromators are placed between an output of each of the lenses and the means for positioning the object under study. Thus one of the crystals is placed with capability of selecting a radiation, having a wavelength lower, and the other crystal is placed with a capability of selecting a radiation, having a wavelength higher, than the absorption line of the element, which presence is checked in the object under study. The device comprises two detectors, each of them being placed after the means for positioning of the object under study so that to receive the radiation, passed through the object under study, and formed by one of crystal-monochromators. The difference of the output signals of the detectors is proportional to the concentration of the element under checking.

Two other geometries, described below, have similar coefficients. In one of them an analytical device includes, besides the source, one more X-ray sources. Thus the radiation of one source has a wavelength lower, and the other one higher, than the absorption line of the element, which presence is checked in the object under study. Only one lens, which can form a quasi-parallel beam, is placed between each source and a means for positioning the object under study. The device includes two detectors, each of them is placed after the means for positioning the object under study so that to receive the radiation, passed through the object under study from only one source. The difference of the output signals of the detectors, as in the previous case, is proportional to the concentration of the element under checking.

In the other geometry the source is made as an X-ray source with an anode with a capability of receiving the radiation with two characteristic wavelengths—lower and higher than the absorption line of the element, which presence is checked in the object under study. One lens is placed between the source and the means for positioning the object under study. The lens is made with a capability of forming a quasi-parallel beam. A rotating screen with cycling windows, closed by filters, is placed in front of or behind the lens; these windows are transparent for one and opaque for the other said wavelength. The difference of output signals of the detectors, conforming two neighboring windows, is proportional to the concentration of the element under checking.

One more type of geometry is characterized by usage of the radiation of the secondary target, placed behind the lens on the radiation way from the source to the object under study. Thus the lens is made with a capability of focusing the source radiation on the secondary target. It allows to irradiate the object under study by a monochromatic radiation of the secondary target, what increases the sensitivity of analysis in cases, when the elements, being checked for presence in the object, have absorption lines, close to the radiation line of the secondary target. The presence of the lens, which concentrates the source radiation on the target, makes possible to compensate the disadvantage of this method (the disadvantage is caused by low intensity of the secondary radiation).

The sensitivity of the method increases in addition in the geometry with the secondary target, which is characterized by the presence of the second lens between the secondary target and the means for positioning the object under study.

The advantages of usage the polarized radiation for irradiation of the object under study, in this case, are the same as in the geometry, described below. In this geometry a lens and a crystal-monochromator, or a multi-layer diffraction structure are placed in succession on the radiation way from the source to the object under study. Thus the lens is made and oriented with a capability of forming a quasi-parallel beam, falling at an angle of 45° on the crystal-monochromator or the multi-layer diffraction structure for forming the polarized radiation by them, and the detector is placed at an angle of 90° to the direction of propagation of the polarized radiation. In this geometry, owing to the polarized selection, the background, caused by the Compton scattered radiation drops out.

The next geometry realizes the method of a phase contrast. In this geometry a lens and a crystal-monochromator are placed in succession on the radiation away from the source to the object under study in the analytical device. Thus the lens is made and oriented with a capability of forming a quasi-parallel beam, falling on the crystal-monochromator at the Bragg angle. The crystal is placed in parallel or with slight deflection on the radiation away from the object under study to the detector. It provides a capability of fixing the phase contrast of areas of the object under study by means of the detector (the areas have different densities and cause different refraction of the radiation, falling on them).

The geometry, typical for medical applications, provides the usage of an X-ray source and embodiment of the means for positioning the object under study with a capability of examining the parts or the organs of a human body.

In particular, when using the analytical device for mammography purposes, an X-ray source has a molybdenum (Mo) anode, and the means for positioning the object under study is made to provide a capability of examining the mammary gland.

Thus the integral lens is placed on the radiation away from an X-ray source with the molybdenum anode to the object under study, the lens is made with a capability of forming a quasi-parallel beam with the cross-section, being enough for simultaneous action on the whole area under study; and the detector is placed to provide the distance, not less than 30 cm, between it and the object under study. The usage of the parallel beam and the choice of the distance provide fine contrast of a gained image without usage of the special means for decreasing the influence of the scattered radiation, excited in the object under study.

One more possible field of application of the suggested analytical device in medical diagnostics is computer tomography.

In the described geometry, providing the usage of an X-ray source and the embodiment of the means for positioning the object under study with a capability of examining the parts or organs of a human body, it is stipulated the opportunity of rotational movement rather each other of the means for positioning, from one hand, the lens, placed between the means and the means for positioning the object under study, from the other hand, and the detector, which output is connected to computer means for processing the results of detection. Thus the integral lens is made with a capability of focusing the radiation, formed by the source, inside the object under study. The focusing point here represents a virtual radiation source, placed inside the object under study, that causes the principal difference from a common scanning computer tomograph, in which the detector absorbs the radiation, passed through the object under study from the source, placed outside the object under study. Due to this the procedure of an image formation of small areas of the object under study can be simplified.

In the suggested invention, related to the device for radiotherapy, the irradiation doze on the tissues, surrounding the tumor, can be decreased by means of focusing the radiation on the tumor, due to what the radiation concentration in healthy tissues, namely on the patient's skin, considerably decreases at the same doze of irradiation on the tumor.

To obtain the result the suggested device, as well as the known one, includes one or more radiation sources, representing the neutral or charged particle flux, as well as the means for positioning the patient's body or its part for irradiation.

As against the known one, the suggested device for radiotherapy includes the lens, placed between each of the sources and the means for positioning, for radiation focusing on the patient's tumor. The lens includes the radiation transporting channels, adjoining by their walls, with total external reflection; the channels are oriented by their input ends with a capability of capturing the transported radiation. The given lens is made as a package of sublenses of different degree of integration. Thus the sublens of the least degree of integration is made as a package of channels for transporting the radiation, which is growing out of the joint drawing and forming of channels bundle at the pressure of the gaseous medium in the space between the channels, being less than the pressure inside the channel of the capillaries, and at the temperature of a softening of the material and splicing the neighboring capillaries. Each sublens of the higher degree of integration is made as a package of sublenses of the previous degree of integration, which is growing out of their joint drawing and forming at the pressure of the gaseous medium in the space between the of sublenses, being less than the pressure inside the channels of sublenses, and at the temperature of a softening of the material and splicing the neighboring sublenses. All sublenses of the highest degree of integration are combined in a unified structure, growing out of their joint drawing (i.e., pulling or stretching) and forming at the pressure of the gaseous medium in the space between the sublenses, being less than the pressure inside the channels of sublenses, and at the temperature of a softening of the material and splicing the neighboring sublenses. The ends of the unified structure are cut and form an input and output ends of the lens.

A nuclear reactor or accelerator may be used as the sources. Quasi-parallel beams of thermal or epithermal neutrons are formed on the outputs of the said nuclear reactor or accelerator.

Thus the used integral lens can contain the curved longitudinal axis for the neutron beam turning.

As it was already mentioned at discussion above, neither with the assembled lenses (lenses of the first generation), nor with the monolithic lenses (lenses of the second generation) it is impossible to realize the channel size of about 1 $\mu$m on the input and of about 0.1 $\mu$m on the output at the exit aperture of 10 cm$^2$ and more, what is necessary for lithography in microelectronics. The parameters can be realized with an integral lens.

The suggested device for contact X-ray lithography contains the soft X-rays source, the lens for transformation the divergent radiation of the source to quasi-parallel (this lens contains the radiation transporting channels, adjoining by their walls, with total external reflection), and the means for positioning the mask and the substrate with the resist, applied on it.

As against the known one, the lens of the suggested device is made as a package of sublenses of different degrees of integration. Thus the lens of the least degree of integration represents a package of radiation transporting channels, which is formed by joint drawing the bundle of capillaries at the pressure of the gaseous medium in the space between the channels of capillaries, being less than the pressure inside the channels of capillaries, and at the temperature of softening of the material and splicing the neighboring capillaries. The sublens of each higher degree of integration is made as a package of sublenses of the previous degree of integration, which is growing out of their joint drawing and forming of at the pressure of the gaseous medium in the space between the sublenses, being less than the pressure inside the channels of the sublenses, and at the temperature of softening a material and splicing of the neighboring sublenses. All sublenses of the highest degree of integration are combined in an unified structure, which is growing out of their joint drawing and forming at pressure of the gaseous medium in the space between the sublenses, being less than the pressure inside the channels of sublenses, and at the temperature of softening a material and splicing the neighboring sublenses. The ends of the unified structure are cut and form the input and output ends of the lens.

It is possible to increase the accuracy of mask imaging on the resist up to the level, being enough for projection lithography in microelectronics owing to the usage of the suggested integral lenses in the device.

The suggested device for projection X-ray lithography, as well as the known one, contains the soft X-ray source, the lens for transforming the divergent radiation of the source to quasi-parallel, intended for irradiating the mask, the means for mask positioning, the lens for X-ray image transmission of the mask on the resist with diminution of the image size, the means for placing the substrate with the resist, applied on it. Thus both said lenses contain the radiation transporting channels, adjoining by their walls, with total external reflection.

As against the known device, at least second of the lenses in the suggested device for the projection lithography is made as a package of sublenses of various degree of integration. Thus the sublens of the least degree of integration is made as a package of radiation transporting channels, which is growing out of the joint drawing and forming of the bundle of capillaries at the pressure of the gaseous medium in the space between them, being less than the pressure inside the channels of the capillaries, and at the temperature of a softening of the material and splicing the neighboring capillaries. The sublens of each higher degree of integration is made as a package of sublenses of the previous degree of integration, which is growing out of their joint drawing and forming at the pressure of the gaseous medium in the space between them, being less than the pressure inside the channels of sublenses, and at the temperature of a softening of the material and splicing the neighboring sublenses. All sublenses of the highest degree of integration are combined in a unified structure, which is growing out of their joint drawing and forming at the pressure of the gaseous medium in the space between them, being less than the pressure inside the channels of sublenses, and at the temperature of a softening of the material and splicing of the neighboring sublenses. The ends of the unified structure are cut and form the input and output ends of the lens.

To decrease the image size, transmitted on the resist, the second of the lenses, used in the device, is made as an axi-symmetric body with a geneatrix, having a knee, and with the input and output ends of channels, being parallel to the longitudinal axis of the lens, and the input diameter of the lens is smaller than the output one. The same relation takes place between the diameters of separate channels for radiation transportation on the input and output of the lens.

The relation of the diameters, which must be considerably more than 1, determines a degree of diminution of the mask image at its transmission on the resist, and, therefore, the degree of miniaturization of the products of microelectronics.

Figure 2:
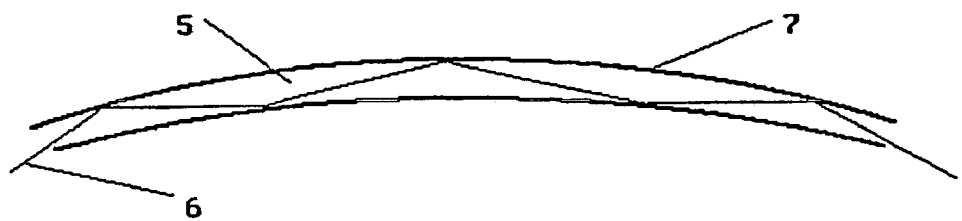
FIG. 2 depicts the process of multiple radiation reflection at its distribution along the channel of transportation.

Referring to FIG. 1, the full integral lens 1 has an input 2 and output 3 focuses, placed on its optical axis 4 in the point of the intersection of the continuations of the axial lines of the radiation transporting channels. FIG. 2 depicts one of these channels. A particle, captured by the input end of the channel, moves in the channels along the trajectory 6, being reflected from the walls 7 of the channel at angles, less than the critical value θc of the angle of the total external reflection. θc is of several mrad. The cross-section of the channels is of micron fractions size order, and their quantity, as it was mentioned, is about 1 million. Therefore the given images are conditional and the scale of the figures is far from the real one.

Figure 3:
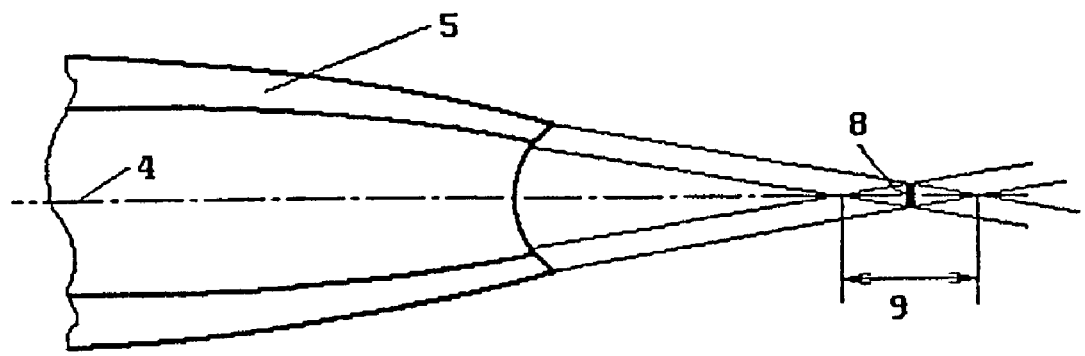
FIG. 3 depicts forming of a focal spot.
Figure 4:
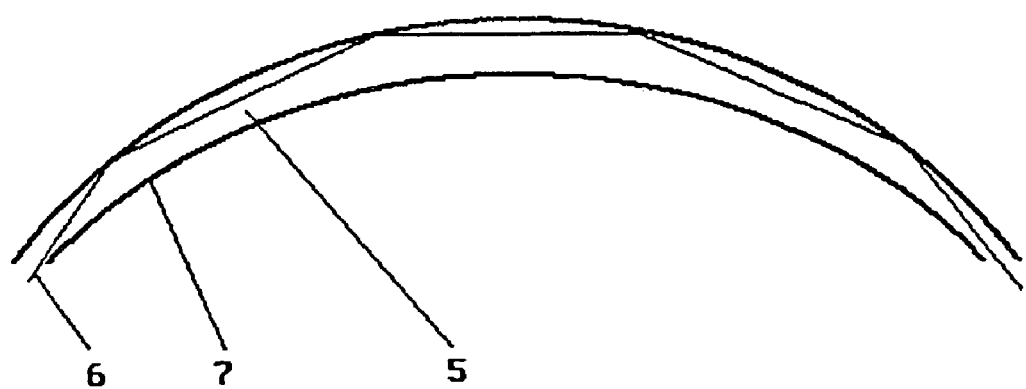
FIGS. 4 and 5 depict the process of multiple radiation reflection at its distribution along the channel of transportation and forming of a focal spot, when the effect of "pressing" of the radiation to the exterior side of the wall of the channel takes place.
Figure 5:
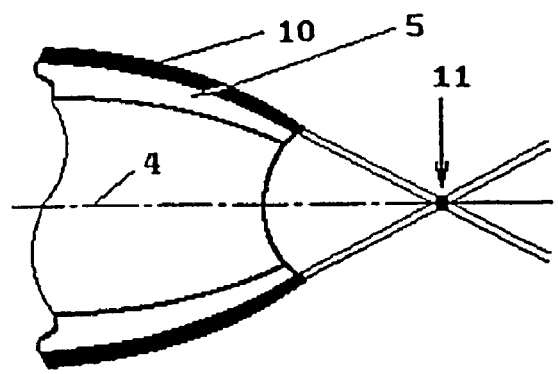

FIG. 3, illustrating the forming of the focal spot by the radiation, exited from the channels 5, depicts the focal spot, which is spread in the lengthwise direction and can have the size 9, considerably exceeding the size 8 in the cross direction. This phenomenon refers to one of the types of aberrations in the optical systems. To decrease this aberration it can be recommended to follow not the traditional requirement of filling the whole cross-section of the transporting channel with the radiation ($\gamma \geq 1$), but visa versa ($\gamma < 1$), or even ($\gamma << 1$), when producing the integral lens. In this case FIG. 4 depicts the character of trajectory 6 of the particle, captured by the channel. Thus the radiation is reflected each time from one and the same wall 7 of the channel 5, and the radiation, as though, "presses" to the wall, filling a small part of the cross-section of the channel. As a result the size of the focal spot is determined by the size of this part of the cross-section of the channel, and the same effect is achieved, as well as at diminution of the section. As to decrease the degree of filling the cross-section of the channel by radiation, with other conditions being equal, it is necessary to decrease the radius of channels curvature, the continuation of the output ends of the channels converge in the focus area at major angels. Owing to this fact the spread of the focal spot in the lengthwise direction decreases, that promotes eliminating the aberration mentioned above. FIG. 5 depicts the described phenomena, where the parts 10, participating in radiation transporting, of the channels 5 are black colored. It is visible, that the sizes of the focal spot 11 are smaller in both directions, than on the FIG. 3.

It can be impossible to follow the requirement ($\gamma << 1$) or ($\gamma < 1$) for the central channels (adjoining the optical axis of the lens), having smaller curvature than peripheral ones. The central part of the lens can be made without the radiation transporting channels (see FIG. 6, where the continuous central part 12 is shaded) or it can be closed with the screen from the source side to except the negative influence of the central channels.

Figure 6:
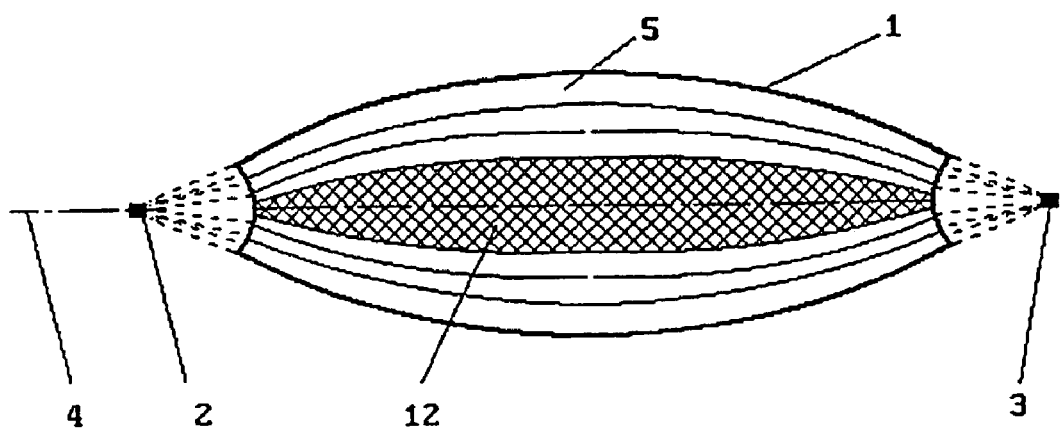
FIG. 6 depicts the full lens, the central part of which does not contain the radiation transporting channels.
Figure 7:
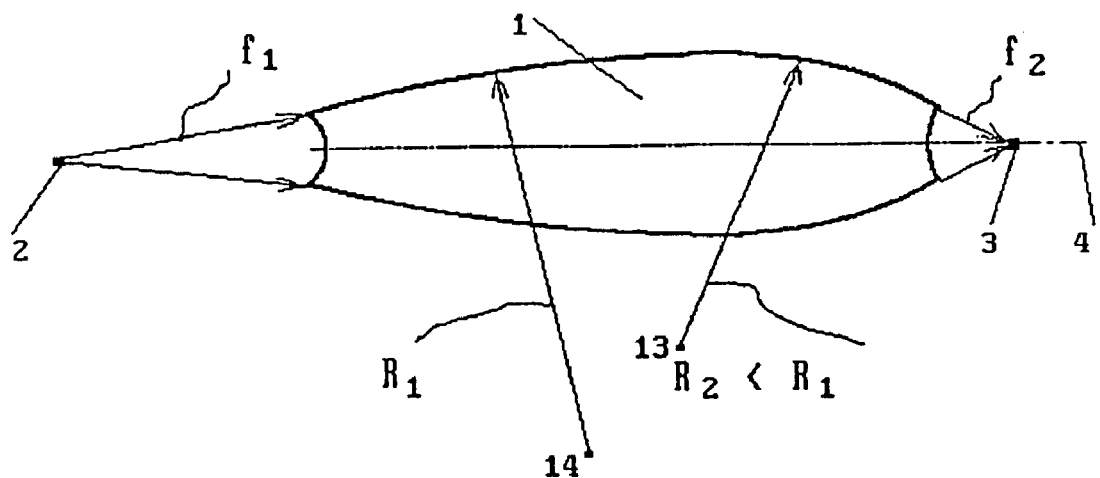
FIG. 7 depicts the full lens with unequal radiuses of curvature of channels from the input and output sides.

Each channel of the symmetrical (with respect to the middle cross-section lengthwise the lens) full lens has the constant curvature radius, the smaller it is (i.e. the channel curvature is larger), the more distanced is the channel from the optical axis 4 of the lens (see FIGS. 1 and 6). The full lens can be made asymmetrical with respect to the section, as it is shown in FIG. 7. The curvature of each channel of the asymmetrical lens is inconstant along its lengthwise. Thus the curvature is larger for the ends of all channels, adjacent to one of the faces, and it is smaller for the opposite ends of the same channels, adjacent to the other face. FIG. 7 depicts the channels, adjoining to the left face and having smaller curvature (larger radius of curvature). The center of curvature can occupy different positions (FIG. 7, positions 13 and 14) for different parts of the channels of the ends.

Figure 8:
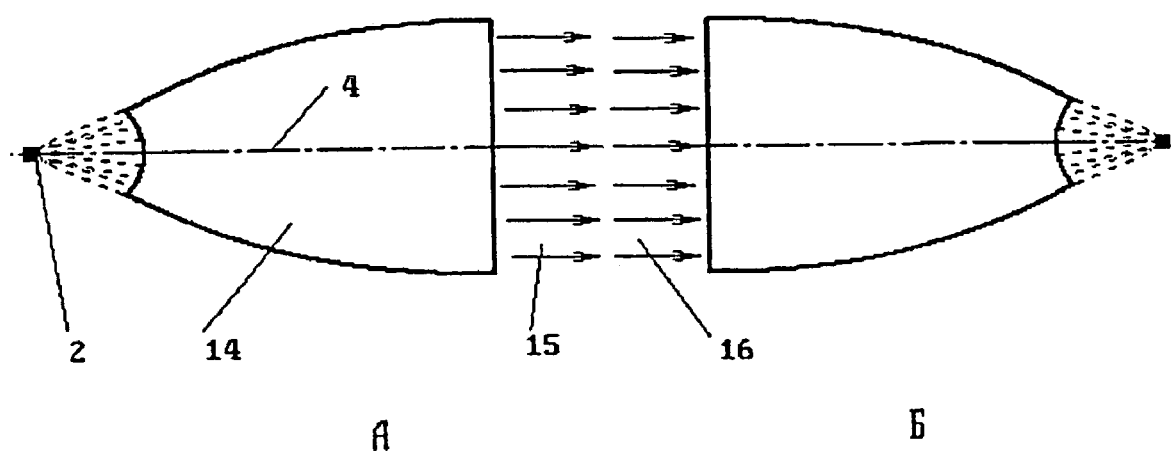

The integral half-lens 14 (FIG. 8a) has only one focus 2 from the side of the smaller face (left one in FIG. 8a). The ends of the channels, adjoining this face, are oriented toward the focus 2. The ends of the channels, adjoining the larger face (right one in FIG. 8b), are parallel to the optical axis 4 of the half-lens 14. If the focus 2 is combined with the point source, the radiation 15 on the output of the half-lens 14 is quasi-parallel. If such radiation 16 is delivered from the major face (FIG. 8b), the ends of the channels, adjoining the smaller face (right one in FIG. 8b), become output ones. In this case the radiation, yielding from the half-lens 14, concentrates in the focus.

The faces of the full lens 1 and the half-lens 14, facing the focuses, can be made sphere-shaped with the center in the corresponding focus, as it is shown in FIG. 1, FIG. 7 and FIG. 8a, b. In this case equal requirements of radiation capture of the point source for all channels are provided.

Figure 9:
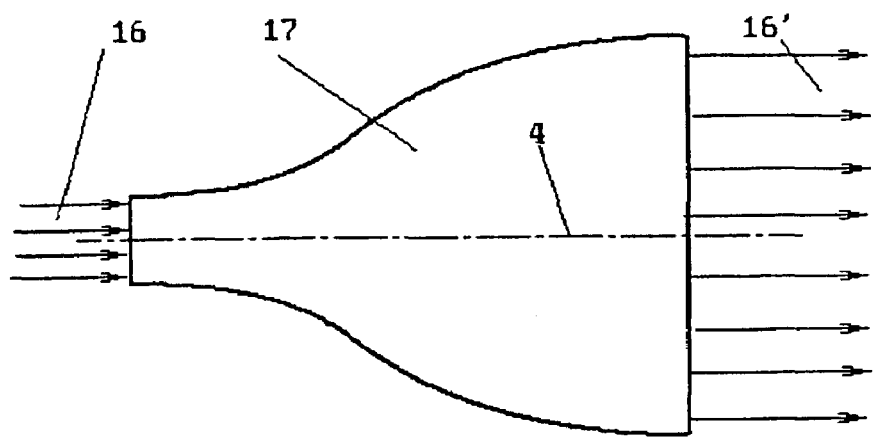

The bottle-shaped lens 17 (FIG. 9) has the ends of the channels, being parallel to the optical axis of the lens, from both faces. Such lens has the form of an axi-symmetric body with the knee of the generatrix. The input quasi-parallel beam 16, falling on the smaller (left one in FIG. 9) is transformed by the lens to the output quasi-parallel beam 16' with the larger section. The cross-section of the output beam, vice versa, decreases as against the input one, when the input radiation is submitted to the larger face (right one in FIG. 9). If the input beam is an image carrier, for instance X-ray image, and the distribution of the radiation intensity in the cross-section of the beam is of character, corresponding the image, so the image scale on the output of the lens changes in appropriate way. The change of the image scale in the integral lens may be as much as two orders. Thus the small diameter of the channels in combination with the absence of the shadowing influence of the envelopes of sublenses (in case, when the lenses are etched in the process of their producing) provides the good quality of reproduction of image details.

Figure 10:
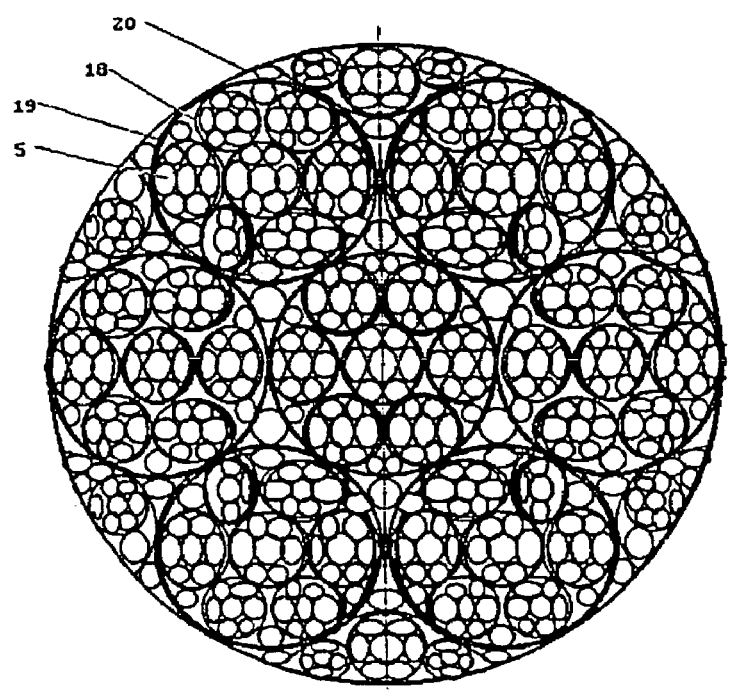
FIG. 10 depicts the schematic picture of the cross-section of the suggested lens.

FIG. 10 depicts the common picture of the cross-section for all types of integral lenses (in view of the note, made above, regarding the convention and scale of the image). This figure depicts the specific case, in which the full lens, as a whole, and the sublens as well have the envelopes. The channels 5 for radiation transporting are inside the envelope 18 of the sublenses of the least (first) degree of integration. Groups of such sublenses, forming the sublenses of the next (second) degree of integration, are placed in the envelopes 19. The package of such sublenses forms the lens as a whole with the envelope 20.

Figure 11:
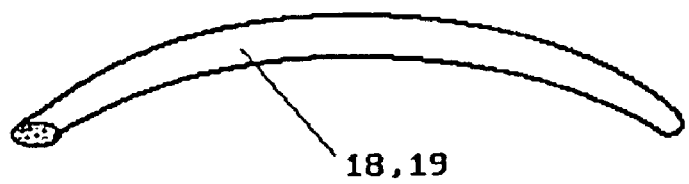
FIG. 11 depicts the schematic picture of one of sublenses.

FIG. 11 depicts the form of one of peripheral sublenses 18, 19 (distant from the optical axis of the lens).

It is necessary to pay attention, that the construction of the suggested integral lens is not simply the result of assembling in a direct sequence of the channels-capillaries in the lenses of the first degree of integration, first of all, then grouping the last ones in the lenses of the second degree of integration, etc. This construction is connected directly with the suggested method of producing, what explains the presence of elements of this method in the characteristic of the construction. Sublenses of any degree of integration and the integral lens do not appear as they are assembled, they result from the realization of the method as a whole after finalizing the forming, which several stages of drawing precede. Neither the lens as a whole, nor the sublenses, being a part of the lens, are not present before the realizing of forming, there are only stocks with straight channels. "Forming", being presented in the characteristic of the integral lens as the feature of the sublenses of different degrees of integration and the lens as a whole, is precisely the above forming, achieved at the final stage of the method. Only after such forming the parts of the integral lens, called the sublenses of the highest degree of integration, and the parts of these sublenses, called the sublenses of the lower degrees of integration, get the features of the lenses. The features differ them from the package of parallel channels. At the same time the produced lens can not be disassembled into sublenses and separate channels. Therefore the sublens, shown in FIG. 11, does not exist off the integral lens as a whole (similarly, the separate electronic components can not be allocated from the integral microchips). The prefix "sub" of the term "sublens" shows that each sublens, not existing independently, carries out the subordinate role in the composition of the lens as a whole. This reason causes the term "a sublens" (but not "a lens") usage to indicate the components of the integral lens.

Thus not only plenty of channels in the lens as a whole and in each of its sublenses, but the circumstances are the basis for the term "integral" usage in the head of the suggested invention, regarding to the lens, and the concept "the degree (level) of integration" for the sublenses characteristic. Only separate capillaries are integrated (combined) in the sublens of the first degree (level) of integration, the elements, being the lenses themselves in the functional relation (the sublenses of the first, second, etc. degrees of integration), are integrated in the sublenses of the second degree of integration and higher.

As it was said above in the characteristic of the suggested invention, relating to the integral lens, the envelopes of the sublenses, which presence is determined by the technology of producing, and which eliminating demands to amplify the method of producing with the operations of etching of these envelopes, play the positive role, as well, increasing the structure stiffness. It is necessary to use for the envelopes the same material, as well as for capillaries, or close to it in value of the thermal expansion coefficient. The removal of the envelopes makes the technological process more difficult, however they deteriorate the lens transparence moderately. Their negative influence on the uniformity of transportation of the radiation intensity along the cross-section of the beam is more essential. Therefore the usage of the lenses free of envelopes, covering the sublenses, is necessary not so much for increasing the transparence of the lens, as much as for eliminating the cause of nonuniformity of intensity transportation along the cross-section of the beam, what can be important in a series of applications.

To produce the lenses, described in the suggested method, the tubular envelope 21 (FIG. 12), for instance glass one, is filled with the stocks, received at the previous stage of the method, and then it is delivered to the furnace 22 vertically by means of the upper drive 23, and it is drawing from the furnace at a speed, exceeding the feed speed, by means of the bottom drive 24. The product 25 with significantly smaller diameter than the diameter of the envelope 21 at the entrance of the furnace is a result of drawing. The temperature in the furnace must be enough to soften the material and splice the neighboring stocks, filling the tubular envelope 21. At the first stage as the stocks, which the tubular envelope is filled by, the capillaries are used, in particular, glass ones, produced from the glass of the same sort, as it was used for producing the envelope. The glass capillaries can be produced with the use of the similar technology by means of drawing of glass tubes with the further cutting them on the capillaries of desired length.

Figure 12:
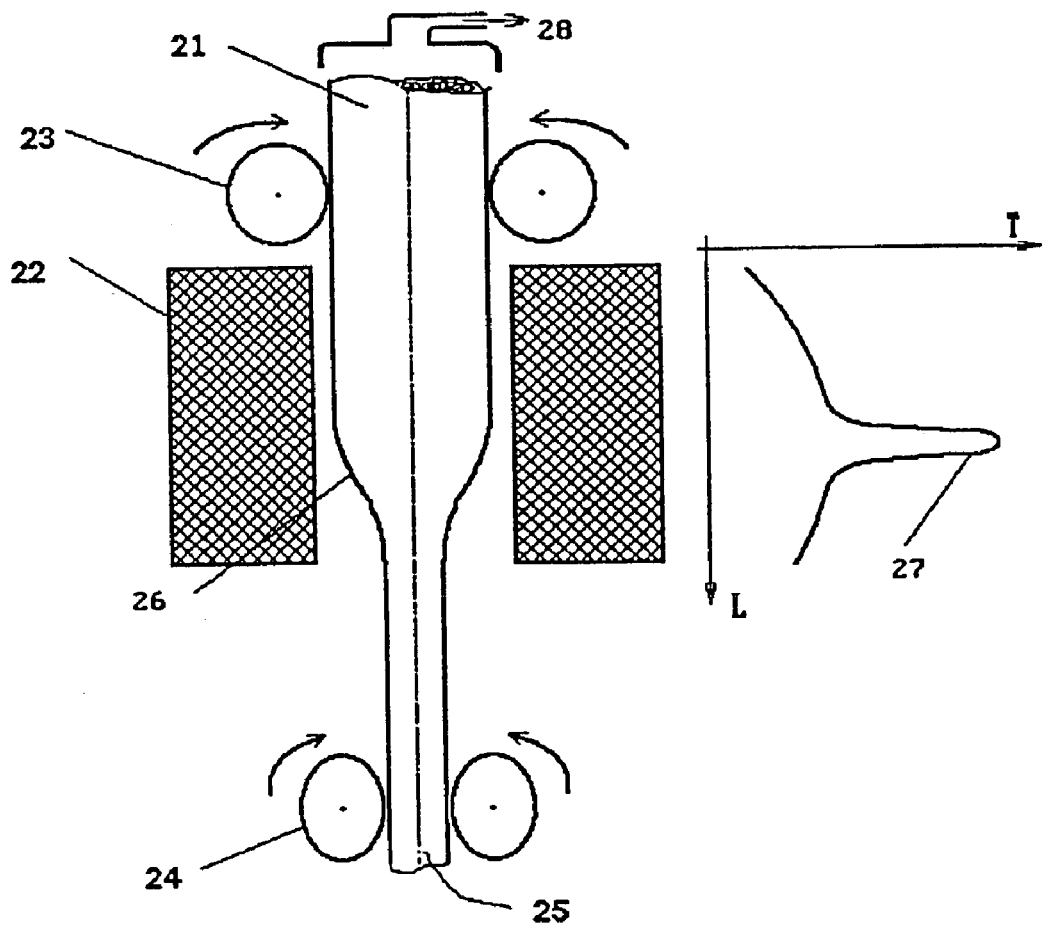
FIG. 12 depicts the scheme of embodying of the drawing operation, when the stocks are produced in the suggested method.

In the process of drawing the axisymmetric temperature field should be formed (FIG. 12 depicts the distribution of temperature T along the furnace height L, having narrow maximum 27). The transition region 26 of the initial diameter of the tubular envelope 21, filled with the stocks, in the smaller diameter is placed in the zone of narrow peak 27 of the temperature distribution along the furnace height.

The pressure between the capillaries should be kept lower than inside the channels of the stocks to prevent the collapse of the capillaries in the process of drawing, accompanying by compression of the stocks, placed in the tubular envelope (eventually, it is important to maintain the higher, than in the space, pressure in the channels of capillaries of the sublenses of the least degree of integration). For this purpose the upper ends of the channels of the stocks should be closed before placing in the envelope (for instance, the upper ends of the stocks should be spliced), and in the process of drawing the gas should be drawn off from the upper end of the envelope filled with the stocks (the draw off is diagrammatically shown in position 28, FIG. 12). It is not necessary to seal the bottom ends of the channels of the stocks, and the envelope, filled with the stocks, because the result, close to the sealing, is obtained by essential diminution of the diameter of the product, emerging from the furnace, in comparison with the initial diameter of the envelope with the stocks, delivered to the furnace from above.

The product, growing out of the drawing, is cut after cooling, and one gets the stocks for the next stage. The tubular envelope is filled with the stocks, and the envelope is drawing similarly the previous stage.

Stocks, obtained at every stage, are acid etchable to remove the material of the envelopes before the tubular shell is filled with the stocks, if it is necessary to produce the lens with the envelope free sublenses.

Figure 13:
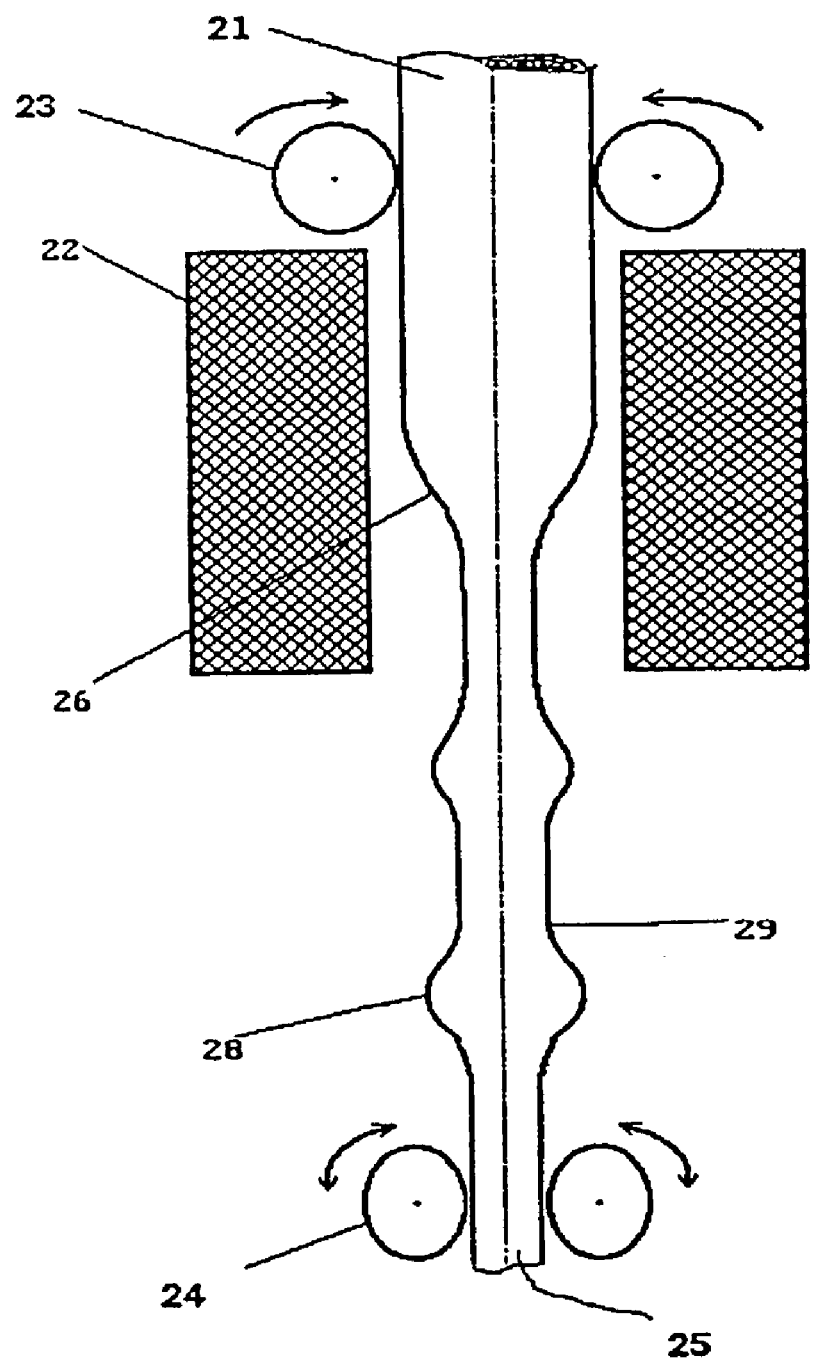
FIG. 13 depicts the scheme of performance of the operation of drawing and forming at the last stage of realizing of the suggested method.

The described stages should be realized several times (usually 3–5), after what the final stage should be realized. At this stage (FIG. 13) the drawing of the product from the furnace is slowed down and then is accelerated again periodically, therefore thickenings 28 are made, connected with tapers 29. The parts of the thickenings, directly adjoining the maximum, are barrel-shaped. The desired curvature of barrel-shaped generatrixes, in which the channels are placed, is obtained by regulation of the variable speed of drawing (i.e. the relation between the speeds of the upper and bottom drives 23, 24), and it is possible to obtain the thickenings, asymmetrical to the maximum as well. At this stage, as well as at the previous stage of producing the stocks, the closing of upper ends of the channels of the stocks before placing them in the tubular envelope and the drawing off the gas from the upper end of the envelope (with the stocks placed in it) is carried out (the drawing off is not shown in FIG. 13).

Figure 14:
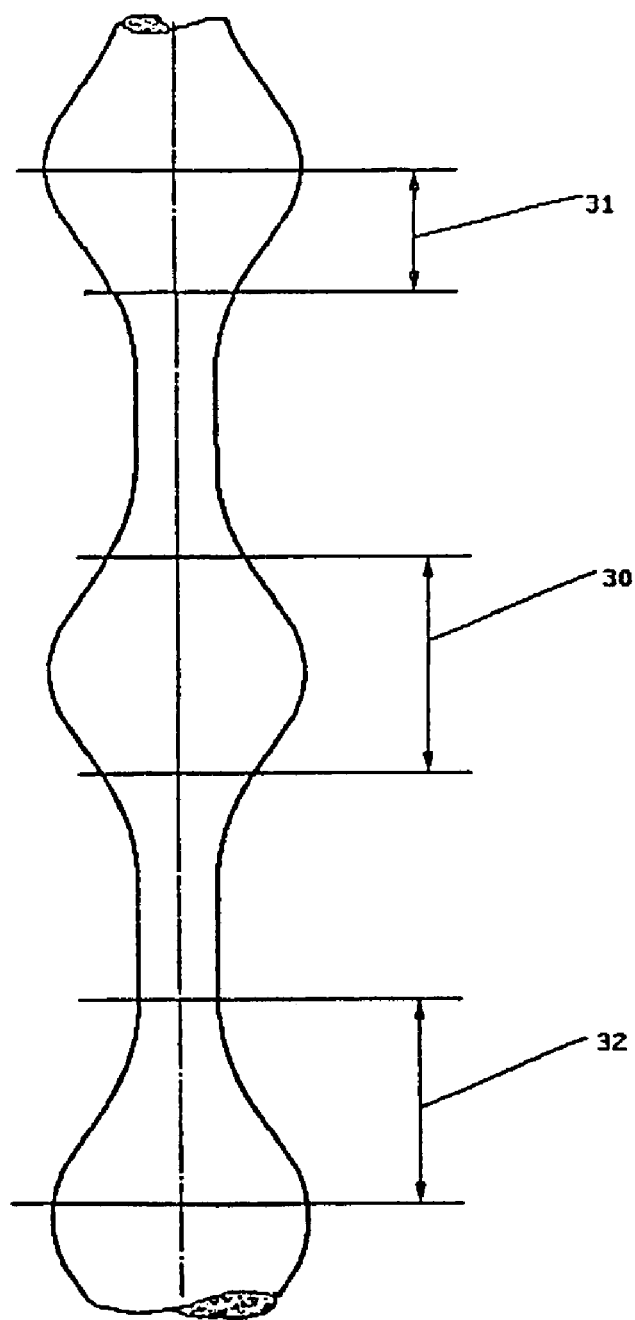
FIG. 14 depicts the schematic picture of the product, which is growing out of drawing and forming at the last stage of the suggested method with the instruction of cut-sections arrangement for obtaining the different types of lenses.

The product with periodic thickenings, obtained at the given stage, (FIG. 14) is cut lengthwise to produce the lenses of the desired type. The positions 30, 31, 32 in FIG. 14 depict the parts of the product, which, after being cut, present correspondingly a full lens, a half-lens or a "bottle-shaped" lens.

When using the integral lenses in the analytical devices for flaw detection, elemental analysis, analysis of the internal structure of the objects, and diagnostics in technology and medicine, huge number of geometries of relative position of radiation sources, analysis object, means for radiation detection, lenses, and other elements is possible. Only some of them in combination with some constructive peculiarities of the analytical device, associated with corresponding geometries, are considered below.

The means for positioning of the object under study (hereinafter it is sometimes called a sample) is one of the constructive elements of the analytical device. As the radiation interacts with the sample by operation of the analytical device, further as a rule precisely the object under study (a sample) is mentioned, and not the means for positioning, though it (and not the sample) is a constructive element of the analytical device.

Figure 15:
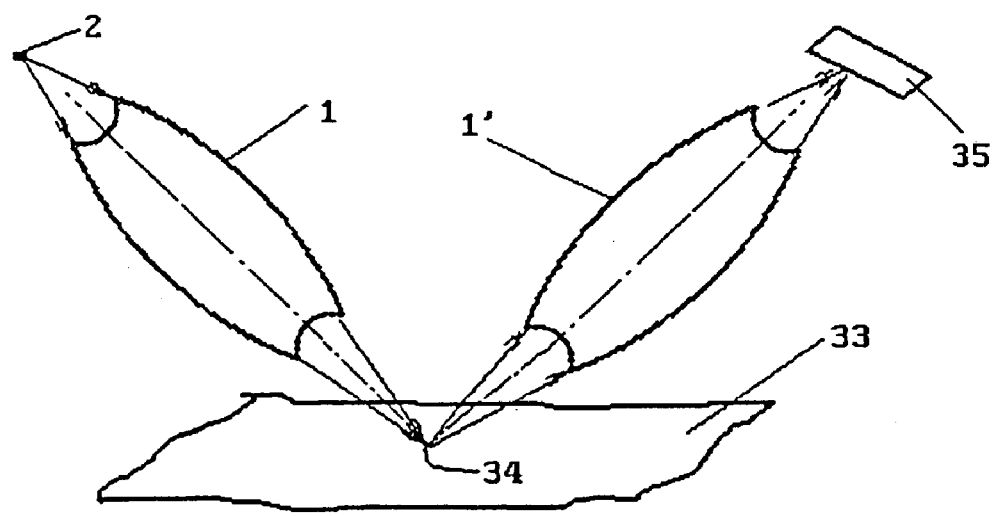
FIGS. 15–24 depict various variants of the geometry of arrangement of the components of the suggested analytical device, used mainly in technical purposes.

High efficiency of analysis, owing to focusing of the source radiation in one point on the surface of the object under study in combination with the radiation capture, scattered by the sample, in some bodily angle with the following radiation concentration on the detector, is obtained owing to the geometry, showed in FIG. 15. Here the full lenses 1 and 1' have combined focus 34, which can scan the surface or interior areas of the sample 33. The detector 35 absorbs the radiation, focused by the second lens 1'. The analysis, using the low-power source 2, can be realized by means of the lens 1', focusing the radiation of the point source 2 on the object of analysis, and the lens 1.

Similar geometry (without the second lens 1') is used in energy dispersion method, when the semi-conductor detector is used. Thus the lens 1 focuses the radiation on the object (sample), the detector 35 is placed close to the sample, and the detector registers both a fluorescent radiation and a radiation, scattered by the sample. In such geometry the integral lens 1 increases the photon flow on the sample, and the detector vicinity to the sample makes it possible to collect more quantity of photons. The lens 1 removes high-energy photons, which create the high background of the scattered radiation, from the source spectrum. The analysis localization is obtained by means of radiation focusing on the small area of the sample 33.

The important specific case of the embodiment of the analytic device is the use of X-ray tubes with a through anode. If the lens with very small focal distance is used (for instance, the lens, in which, at the factor $\gamma \ll 1$, the effect of "pressing" to the exterior side of the transporting channels arises), so such lens can be placed closely to the through anode. Thus the lens can be made small-sized, conserving the wide capture angle simultaneously. Such combination is especially effective (the tube with through anode plus the integral lens), when the anode is microfocal (0.1–100 microns). As the solid angle of the radiation of the through anode is wide (it is close to a hemisphere), the tube with the through anode can be effectively used simultaneously with some lenses, and each lens gathers the radiation from the part of the solid angle.

It is necessary to mention, concerning both the described schemes, and those, which will be described below, that these schemes contain minimum elements, being enough to realize the analysis by means of the device (i.e. to get some information about the object under study). To provide the receiving the information, handy for immediate use, to improve the receiving the clear information operatively, etc., the analytical devices are supplemented with the means for processing and presenting the information, which are connected to the detector output. The means realize transformation of the output signals of the detector, visualization of the signals synchronously with the mechanical movements of the elements of the analytical device, etc. The synchronization demands the connection of the means for processing and presenting the information with the means for realizing the movements. The means for processing and presenting the information, used with the analytical devices, are known. And their functions and structure do not depend on the way, which the signals, carrying the information about the object under study, were received by. For this reason the detector output is accepted to view as the output of the analytical device (the detector output is sensitive to the radiation, which is growing out from the source radiation and the object under study interaction, therefore the detector output carries the information about the features of the object under study).

Figure 16:
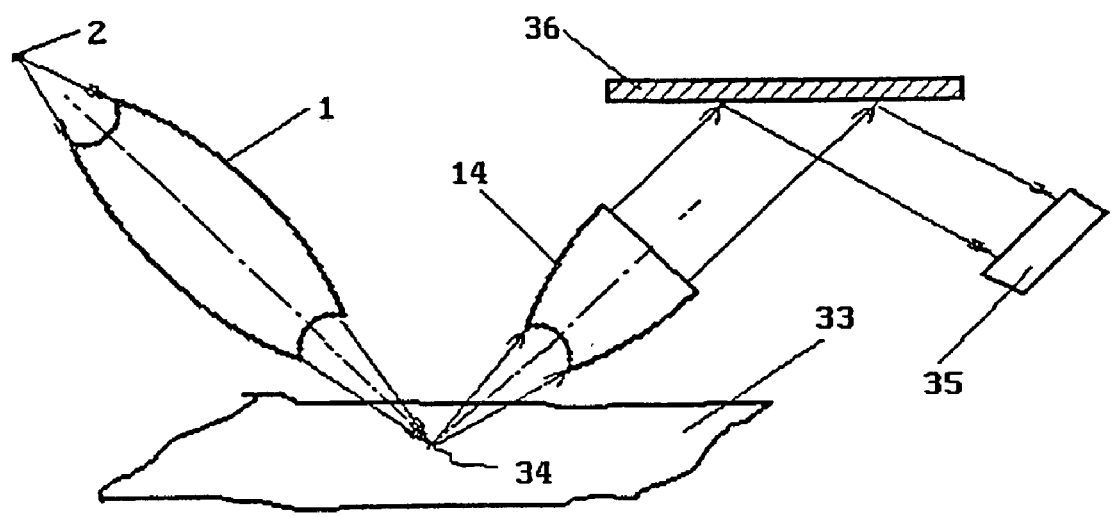

In the next considered geometry (FIG. 16) a means for monochromating the radiation, excited in the sample 33, is used (crystal-monochromator 36). The radiation is monochromated owing to the conditions of reflecting of the parallel beam from the crystal-monochromator are met in the very narrow interval of particle energies. To form a parallel beam and, simultaneously, to gather a radiation, scattered by the object under study, the half-lens 14 is used. Its focus is combined with the focus of the full lens 1, focusing the radiation of the point source 2 in the point 34 of the object under analysis. Varying the particle energy, falling on the detector 35, makes possible to study in more details the features of the sample by means of change of angular position of the crystal-monochromator, in particular to study the sample on presence of definite chemical elements.

Figure 17:
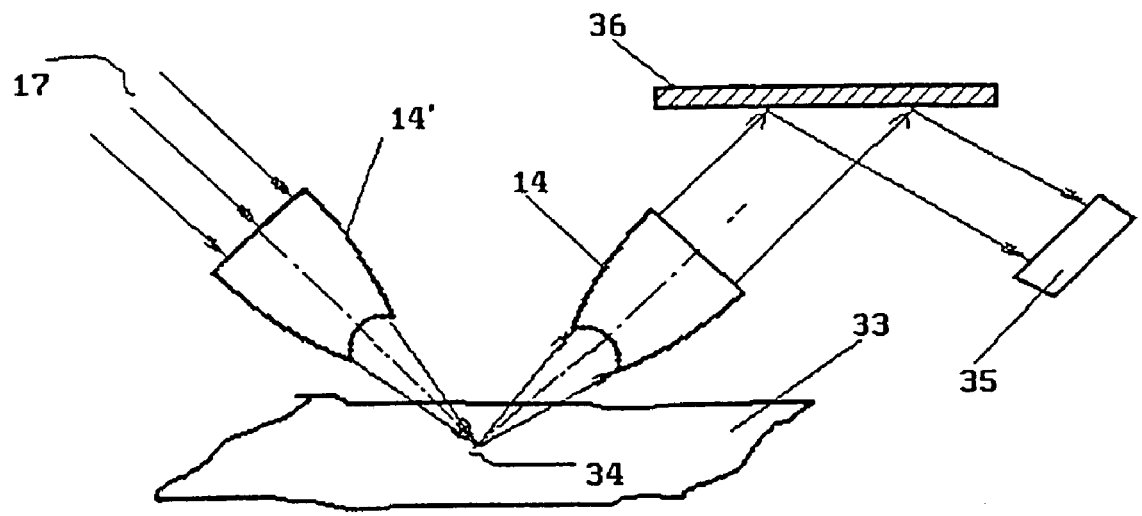

The geometry in FIG. 17 differs from the previous one in that a source of quasi-parallel radiation 17 (for example, a synchrotron source) is meant to be used instead of a point source. The half-lens 14' focuses the radiation of this source in the point 34, being at the same time a focus of the half-lens 1, which forms a quasi-parallel beam for the monochromator 36.

A common peculiarity of the following two geometries (FIG. 18 and FIG. 19) is the fact, that radiation, passing through the sample, and the radiation, excited in the sample by acting of monochromatic radiations of two close wavelengths, are studied simultaneously.

Figure 18:
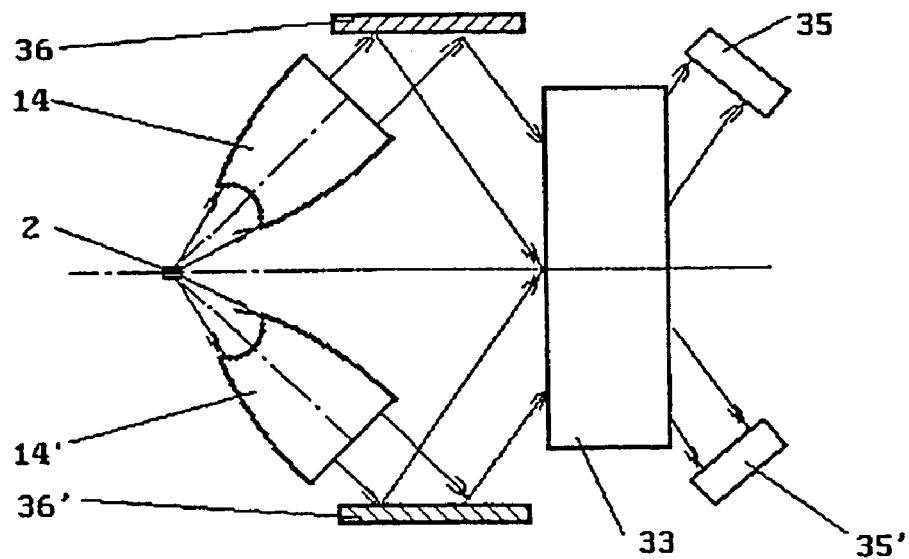

In the geometry in FIG. 18 such radiations are obtained from one broadband point source 2 by means of two crystal-monochromators 36 and 36', irradiating them with parallel beams, formed by half-lenses 14 and 14', which common focus coincides with the source 2. To prevent the direct hit of the radiation of the source 2 on the sample 33 an absorbing screen (it is not shown in the drawing) must be set between them. The output signals of the detectors 35 and 35' differ in that degree, in what the reaction of the object under study is different, when the object is irradiated with particle fluxes of different, but close energies. Difference of these signals gives the information only about such difference. Therefore if one of the energies is higher, and the other is lower than the absorption line of the element, which presence it is necessary to detect in the sample, the sensitivity of the device is very high owing to the exclusion of all other factors influence on the difference of output signals of the detectors 35 and 35'. The given geometry can by used, for example, in angiography, when iodine is injected in a patient's blood, and it allows to increment the sensitivity of the method approximately on two orders in comparison with the case, when the lenses, which form a parallel radiation, falling on the monochromators, are absent, and the distance between the monochromators and the source must be increased.

Figure 19:
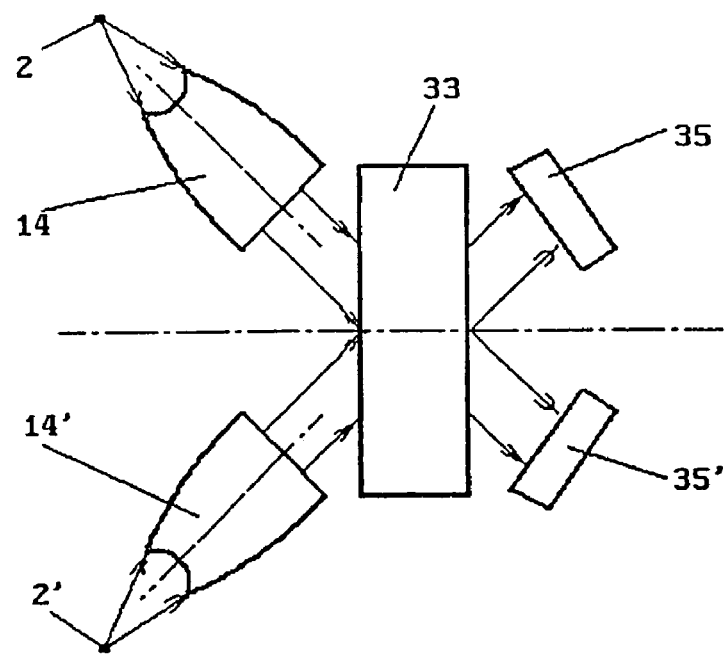

In the geometry in FIG. 19, realizing the same principle, two different point sources 2 and 2' are used to obtain particles with different, but close energies. The radiation of these sources has clearly defined characteristic lines: higher and lower than the absorption line of the element, to be detected. The radiation of both sources is transformed, by means of the half-lenses 14 and 14', to quasi-parallel one, acting directly on the sample 33.

Figure 20:
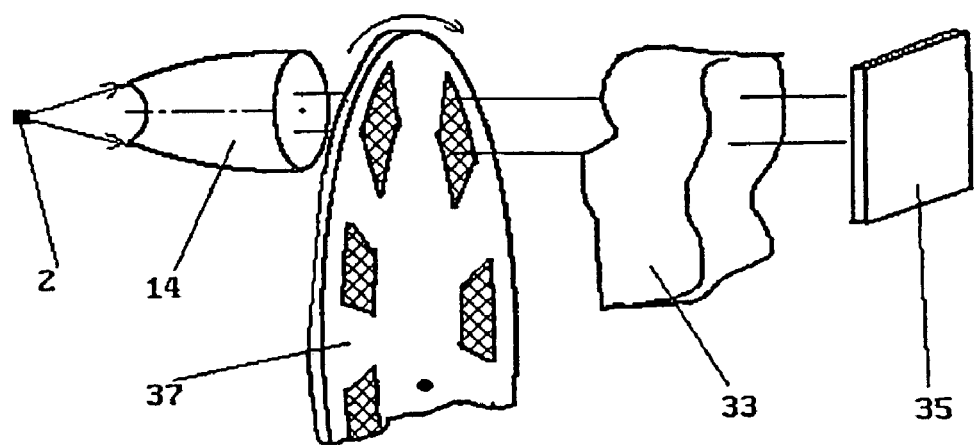

FIG. 20 depicts one more variant of realizing of the same principle. In this geometry radiations with two energies, acting on the sample 33, are formed alternately as a result of radiation transmission of the same source 2 through the alternating filter-windows of the rotating screen 37. These windows alternate in such a way, that they are transparent for one wavelength and opaque for the other wavelength of the radiation, which must act on the object under analysis. The rotating screen 37 with windows can be placed both after the half-lens 14, which transforms a divergent radiation of the source to quasi-parallel (FIG. 20 depicts this case), and before the half-lens 14. The difference of the output signals of the detector 35, corresponding to two adjacent positions of the rotating screen 37, can be used in the same way as in the geometries in FIG. 18 and FIG. 19.

Figure 21:
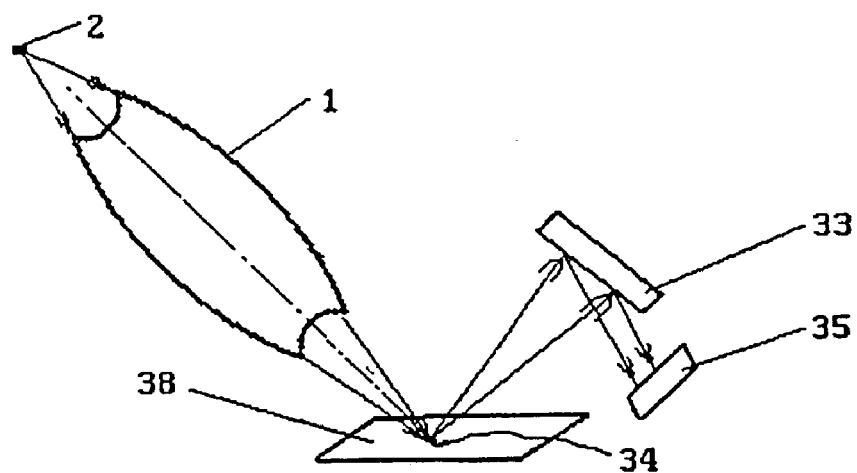

In the geometry in FIG. 21 the usage of the secondary target 38 is provided for obtaining a monochromatic radiation with the wavelength, defined by the features of the target. A weakness of the known devices with a secondary target is rather low intensity of a secondary radiation. The influence of the weakness is removed due to the usage of the lens 1 in the described geometry. The lens 1 concentrates the source radiation on the target in a small area 34 of the focal spot. The radiation of the secondary target 38 falls on the object under study 33, where fluorescence radiation, which falls on the detector 35, arises. This geometry makes possible to irradiate the object under study with rather intensive monochromatic radiation of the secondary target.

Figure 22:
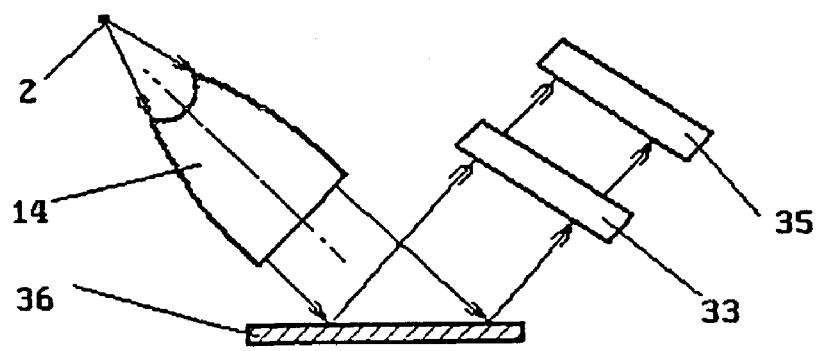

In the geometry in FIG. 22 the sample 35 is irradiated with a monochromatic radiation as well, but in this case the crystal-monochromator 36 is the radiation source, not the secondary target. A parallel beam, required for a monochromatic radiation forming, is formed of the divergent radiation of the broadband source 2 by the half-lens 14. A wavelength (particle energy) of the radiation, acting on the object under study, can be changed by varying an angular position of the crystal-monochromator.

Figure 23:
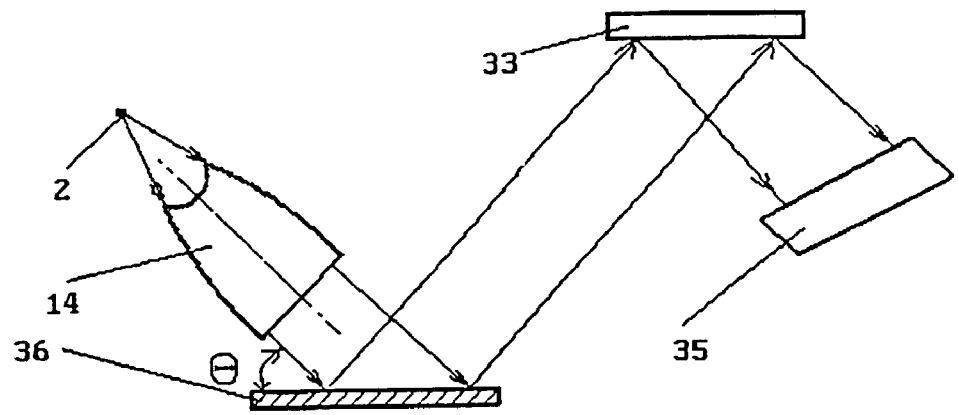

In the geometry in FIG. 23 the crystal-monochromator 36, irradiated by an quasi-parallel beam, formed by the half-lens 14, is used as well. A feature of the crystal-monochromator to form a polarized radiation is used in this geometry. For this purpose the quasi-parallel beam is directed to the crystal-monochromator 36 at $\theta=45°$ angle. A diffracted radiation from the crystal-monochromator 36 falls on the sample under study 33, and the radiation from the sample under study 33 falls on the detector 35, positioned at a 90° angle to the direction of propagation of the polarized radiation of the crystal-monochromator 36. Due to this polarized selection takes place, and the detector 35 is free of the background influence, produced by the divergent Compton radiation, arising in the sample under study when the radiation from the crystal-monochromator 36 acts on it.

In this geometry a target made of light metal (for example, beryllium (Be)) can be used instead of the crystal-monochromator.

Figure 24:
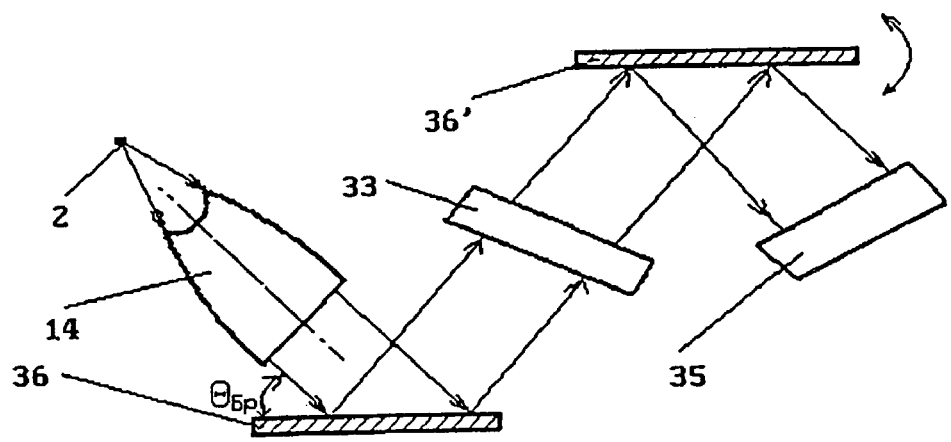

The geometry in FIG. 24 is used to realize the method of a phase contrast. In this method a sample is irradiated with a monochromatic radiation, formed by the first crystal-monochromator 36, and a parallel beam for this purpose is formed of the divergent radiation of the source 2 by the half-lens 14. The radiation falls on the crystal-monochromator 36 at a Bragg angle $\theta_{Br}$. The second crystal-monochromator 36', identical to the first one, is positioned after the sample with a capability of varying its angular position in small limits with respect to the position, parallel to the first one. When there are some irregularities in the sample, which differ in density from the neighboring areas, a radiation refracts in such irregularities, passing through them, differently than in the neighboring areas. It can be fixed when a signal appears on the output of the detector 35 at a definite position of the second crystal-monochromator. The sensitivity of the method of the phase contrast is much higher in comparison with the immediate fixation of differences of planes (for example, differences of radiation intensities, passed through the neighboring areas of the object with different, but close densities). The usage of lenses makes possible, without increasing the source power, to work at increased magnitude of intensity of the quasi-parallel radiation, falling on the crystal-monochromator, and the radiation, falling on the detector.

It was already mentioned above (see the usage of the analytical device in angiography) that the analytical device can be used in medical diagnostics.

Figure 25:
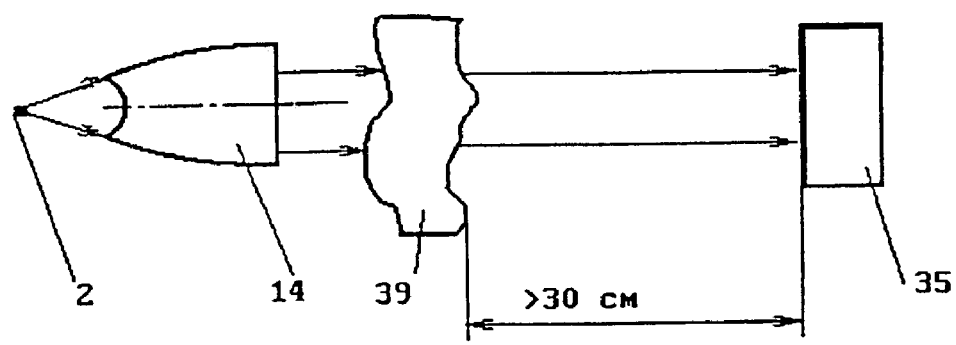
FIG. 25 depicts the usage of the integral lens in the analytical device, intended for medical diagnostics.

FIG. 25 depicts the usage of an integral half-lens in the analytical device, solving problems of medical diagnostics. The object under study 39 (a part or an organ of a human body) is irradiated with a quasi-parallel radiation, formed by the half-lens 14 from the divergent radiation of the source 2, being placed in the focus of this lens. The detector 35 receives two-dimensional density distribution of the radiation, passed through the object 39 (this two-dimensional density distribution of the radiation is interpreted as density distribution of the object in the corresponding projection). A distinction of the given geometry is that the detector must be placed far enough from the object (for a distance of not less than 30 cm). Due to the fact, that the object is irradiated with a quasi-parallel beam, the distance of the detector practically has not an effect for a desired signal level of densities distribution of the object. However in this case the influence of the divergent radiation, arising in the object, sufficiently attenuates, due to what an image contrast range increases.

In this case an integral lens is made with a capability of forming a radiation field of 20×20 cm² order size. If the detector is placed at the mentioned distance from the object, so it is no need to use any means for suppressing the divergent radiation in this geometry. Thus both problems are solved: spatial resolution and doze problems. Let, for example, the detector is at the distance of 50 cm from the object. If the resolution is equal to $10^{-4} \times 50 = 50 \times 10^{-3}$ cm=50 $\mu$m the beam divergence will be equal to $10^{-4}$ rad. At the same time an omnidirectional radiation, diverged in the object, reaches the detector with significant (in more than 30 times) attenuation at the distance of 50 cm from the object. Therefore it is possible to do without antiscattering rasters, which usage in order to increase the image contrast range mates with the increase of the radiation dose.

Use of integral lenses makes possible to solve the problems of early diagnostics of oncologic diseases due to the obtainable resolution of 50–100 $\mu$m order. It is appropriate to use an X-ray tube with a molybdenum (Mo) anode (E=17.5 keV) as a source in mammography researches.

Scanning computer tomography is one more promising field of usage of analytical devices with integral lenses in medicine. Modern tomographes provides the image of the density distribution of tissues of a human organism by registration of the radiation intensity, passed from the source to the radiation detector. To calculate the density distribution with the high resolution in one other section it is necessary to irradiate this section many times (usually, more than one hundred) at different angles. Thus the dose is usually high, of 1 R order.

Figure 26:
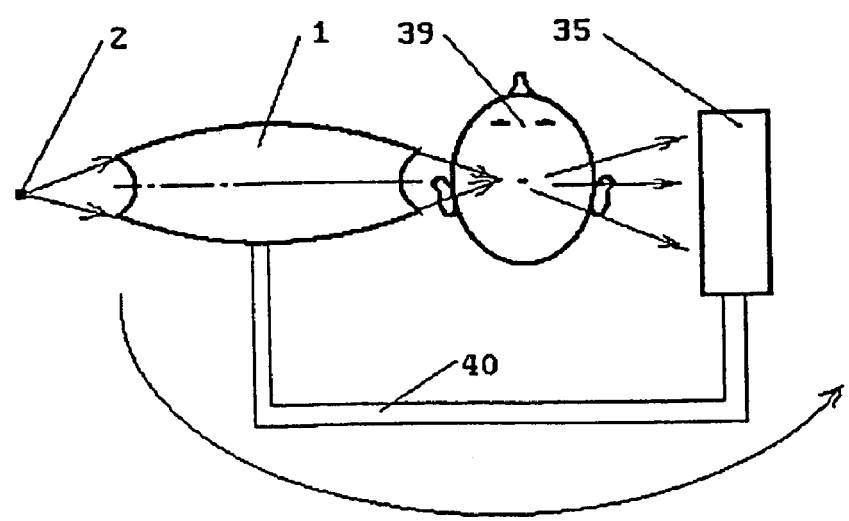
FIG. 26 depicts the usage of the integral lens in the analytical device, used in computational scanning tomography.

The usage of an integral lens with the high level of the radiation focusing provides to change the situation efficiently. As it is shown in FIG. 26, a full lens 1 is placed between a source 2 and a patient 39 so that a second focus is placed inside the area under study. The detector 35, as usual, is on the other side of the patient and it is directed to the radiation yield. The point, the radiation is focused in, acts as a virtual radiation source, placed inside the object under study. Due to this and small sizes of such source, geometric blurriness of the radiation from the source decreases sufficiently. The blurriness is expressed by the formula:

$$U=bd/l,$$

where b—source size, d—a distance from the object to the source, l—a distance from the object to the detector.

When the source is outside the object, d and l are of same order, and blurriness U is of same order with b, i.e. with the source size. If the source is inside the object and placed close to the defect to be detected (here it is a tumor), so d<<l, what explains decreasing of the blurriness of the source.

Due to the small size of a focal spot of an integral lens the blurriness decreases more, what allows to make less irradiations to obtain the sufficient accuracy of the image reconstruction. Due to the possibility of alignment of a focus with any desired point inside the area under study a procedure of the image formation when examining a small object can be simplified. For example, if it is necessary to examine an area of 1 cm² size order of lungs, an output focus of a lens can be placed directly close to this selected area. The focus can be displaced in this area with an accuracy, being equal to the focal spot of the lens. If, for example, a focal distance is 20 cm, so this focal spot is of 0.1 mm size order at the energy 50 keV, when $\theta cr \approx 5 \cdot 10^{-4}$ rad.

FIG. 26 depicts the geometry where an element 40 conventionally represents a presence of rigid connection between a source 2, a full integral lens 2 and a detector 35. At tomography examination these three objects must rotate respectively to a means for patient positioning 39 as an integral part (a variant of rotating of the means for positioning together with a patient, when the source 2, the lens 1 and the detector 35 are fixed, is possible as well).

Figure 27:
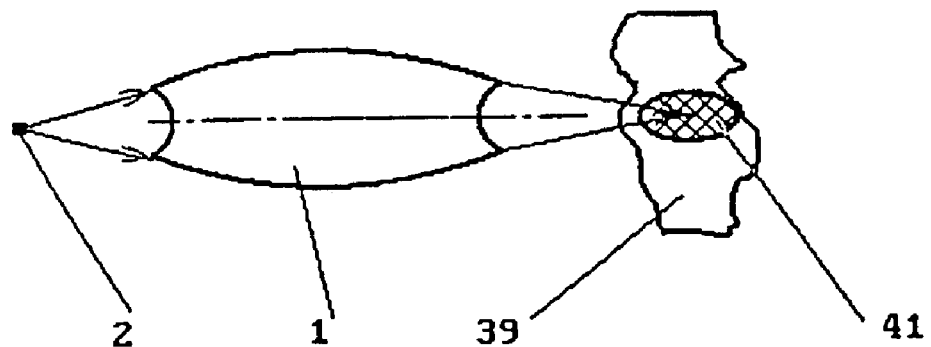
FIGS. 27 and 28 depict the usage of the integral lens in radiotherapy.
Figure 28:
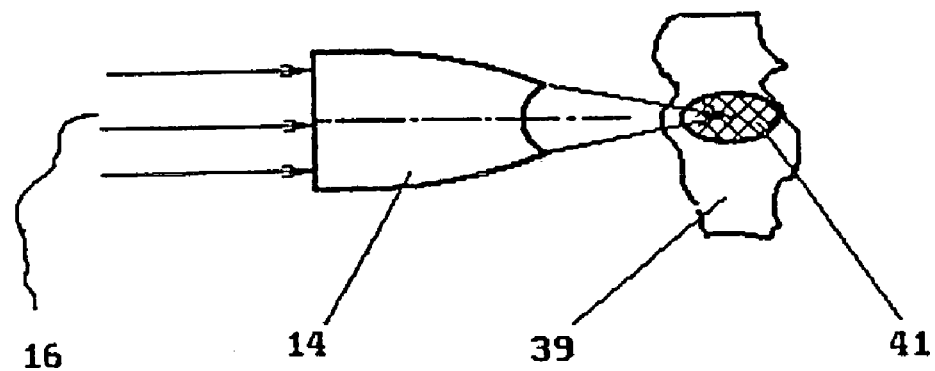

FIG. 27 and FIG. 28 depict the usage of integral lenses in radiotherapy, when obtained result is provided by their higher indexes, such as a size of a focal spot and a focal distance, which defines a size of a focal spot with other things being equal. FIG. 27 depicts a device for radiotherapy, a point source 2 is used in, and FIG. 28 depicts a source of parallel radiation 16, for example an output of a nuclear reactor or accelerator, forming quasi-parallel beams of thermal or epithermal neutrons. The radiation is directed to the patient 39 and it is focused inside the tumor 41. A neutron beam extracts from the reactor, and to direct the beam for usage in the device for radiotherapy it is necessary to turn it by means of a lens (not only integral one) with a curved longitudinal axis.

Providing a high intensity irradiation on a tumor in combination with a low irradiation of surrounding tissues and skin is a serious problem in radiotherapy. It is necessary for this purpose to cross the beams on the tumor at wide angles. The wider are these angles, the larger area of the skin surface and tissues, surrounding the tumor, is covered by the radiation before it reaches the tumor.

An integral lens as a means for focusing the radiation, in particular, the lens, described above, where an effect of radiation "pressing" against the external sides of the channels walls takes place, has precisely those features, which are necessary to solve these problems: it can provide high quality of focusing at a considerable ratio of an output aperture to a focal distance (the latter feature contributes to wider angles of crossing of the beams, which converge at focusing).

The suggested device can comprise some lenses, irradiating the tumor from different positions, to create the large doze gradients on the tumor. A system of lenses can be made with a capability of being displaced with maintenance of the cross of the beams, formed by lenses, on the tumor.

Experiments, carried out, show that even at small energies of 25–30 keV order on depth of 30 cm a doze on the tumor can exceed a doze on the surface. Water phantom of 1–5 cm thickness were used in the experiment.

Figure 29:
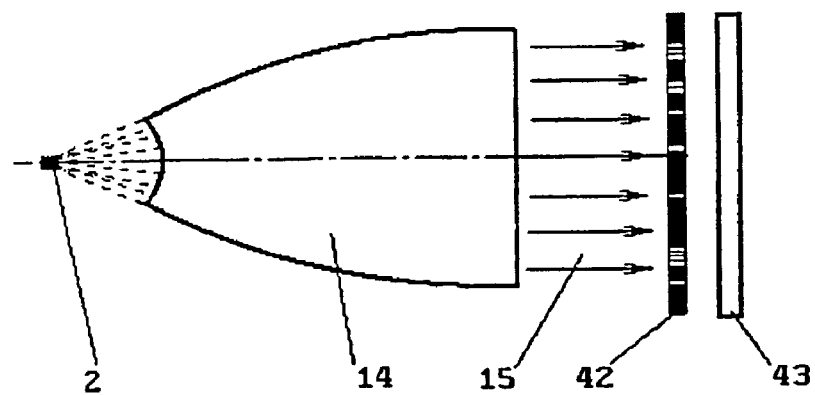
FIGS. 29 and 30 depict the geometry of arrangement the components of the suggested devices for contact and projection lithography.
Figure 30:
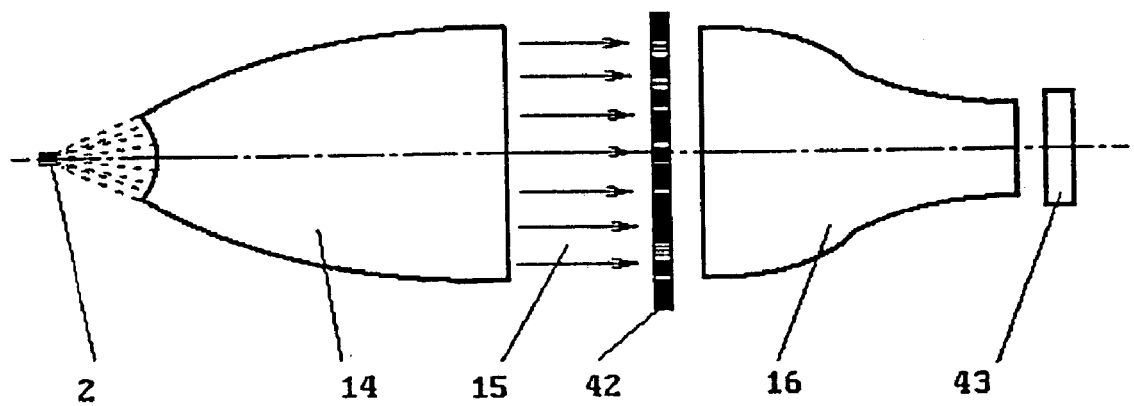

FIG. 29 and FIG. 30 depict schematically the devices for a lithography, the suggested integral lens can be used in as well.

The first one, intended for a contact lithography, comprises a means 43 for a resist and substrate placing. This means is placed close to a means 42 for a mask placing. The latter is placed opposite an output face of the integral half-lens 14, which forms a quasi-parallel beam from the divergent beam of the source 2. In this case a homogeneity of a quasi-parallel beam, i.e. a steadiness of the radiation density along its cross section, is very important. Therefore X-ray lithography is a field, where it is necessary to use integral lenses, comprising sublenses without envelopes.

A device for projection lithography differs from the considered one, that a "bottle shaped" lens 16, faced its smaller face to the means 43 for a resist and substrate placing, is placed between the means 42 for a mask placing and the means for a substrate with a resist placing. The size of the larger face of the lens approximates that of the output end of the half-lens 14. A presence of the "bottle shaped" lens 16, oriented in the manner, provides image transmission of the mask to the resist with decreasing. The degree of decreasing of the image scale is defined by a relationship of the input and output diameters of the lens. A relationship of diameter of the separate channels (capillaries) on the input and output of the lens is the same. As this relationship can be much more than 1, the elements of microelectronics of small sizes can be obtained when using a device for projection lithography. Usage of sublenses without envelopes in the "bottle shaped" lens 16, used in the device for the projection lithography, is important in a greater extent than in the half-lens 14.

In summary, it should be further emphasized that going from the monolithic lenses and the lenses, made as an assembly of microlenses to the integral lenses as a new generation of means for high energies radiation controlling not only provides the increase of indexes accuracy of means, including such lenses, according to the indexes of lenses. In some cases this going makes possible to produce devices, acceptable for practical use (being transportable, suitable for hermetization when used in corrosive medium, and having acceptable cost). In the past the sizes, cost, etc. of the lenses, as well as the impossibility of usage of simple and cheap radiation sources prevent from producing the devices.

While the invention has been described in terms of a single preferred embodiment, those skilled in the art will recognize that the invention can be practiced with modification within the spirit and scope of the appended claims.

I claim:

1. A method for producing lenses for transforming radiation representing a neutral or charged particle flux, including radiation transporting channels with the use of a total external reflection in them, having two or more stages of stocks which produce, at each stage, a tubular envelope filled with earlier made stocks, wherein thin-walled capillaries are used at a first stage, and at each further stage the stocks are used for subsequent stages to complete a product, the method comprising:

the stocks, resulting from a given stage, are produced by cutting the product, emerging from the furnace, lengthwise, wherein at an end of the stage of stocks a tubular envelope is filled with the stocks, obtained at this stage, and they are jointly drawn in the furnace at a feed speed maintained slower than an exit speed of the product from the furnace, and a relationship between the feed speed and exit speed of the product is periodically changed to form barrel-shaped thickenings on the product emerging from the furnace, then lenses as parts of the product are produced from the product by cutting it lengthwise, and the lenses include only one thickening, wherein at all stages the tubular envelopes, made of a same material as the capillaries, or a material having substantially the same thermal extension coefficient, are used and the processes of the tubular envelopes drawing with the stocks, filling the envelopes, occurs while a pressure of the gaseous medium in the space between them is less than the pressure inside channels of the stocks, at a temperature of the material that softens and splices neighboring stocks.

2. A method according to claim 1, wherein during the process of a thickening forming a drawing speed is regulated to obtain the desired form of a cross-section of lenses.

3. A method according to claim 2, wherein for producing full lenses, a cut-off of the product drawn from the furnace occurs on each side of a maximum cross-section of a thickening at a distance from it, that is less than a distance to the point of a knee of a thickening's generatrix.

4. A method according to claim 2, wherein for producing half-lenses, a cut-off of the product drawn from the furnace occurs on sections of maximum thickening, and on each side of a maximum cross-section of a thickening at a distance from it, that is less than a distance to a point of a knee of a thickening's generatrix.

5. A method according to claim 2, wherein for producing lenses having an axi-symmetric body defined by a generatrix having a knee, and the ends of the channels, being parallel to the longitudinal axis of each lens, the cut-off of the product drawn from the furnace occurs on the sections of maximum thickening, and on each side of the thickening, in sections located on the other side of a-knee of the generatrix, on the parts of the product where its diameter is constant.

6. A method according to claim 1, wherein for producing full lenses, a cut-off of the product drawn from the furnace occurs on each side of a maximum cross-section of a thickening at a distance from it, that is less than a distance to a point of a knee of a thickening's generatrix.

7. A method according to claim 1, wherein for producing half-lenses, a cut-off of the product drawn from the furnace occurs on sections of maximum thickening, and on each side of a maximum cross-section of the thickening at a distance from it, that is less than a distance to a point of a knee of a thickening's generatrix.

8. A method according to claim 1, wherein for producing lenses having an axi-symmetric body defined by a generatrix having a knee, and the ends of the channels, being parallel to the longitudinal axis of each lens, the cut-off of the product drawn from the furnace occurs on the section of maximum thickening, and on each side of the thickening, in sections located on the other side of a knee of a generatrix, on the parts of the product where its diameter is constant.

9. A method for producing lenses for transforming radiation representing a neutral or charged particle flux, including radiation transporting channels with a use of a total external reflection in them, the method and two or more stages of stocks which produce, at each stage, a tubular envelope filled with earlier made stocks, wherein thin-walled capillaries are used at a first stage, and at each further stage the stocks are used for subsequent stages to complete a product, the method comprising:

the stocks, resulting from a given stage, are produced by cutting the product, emerging from the furnace, lengthwise, wherein at the end of the stage of stocks the tubular envelope is filled with the stocks, obtained at this stage, and they are jointly drawn in the furnace at a feed speed maintained slower than an exit speed of the product from the furnace, and the relationship between the feed speed and exit speed of the product is periodically changed to form barrel-shaped thickenings on the product emerging from the furnace, then the lenses as parts of the product are produced from this product by cutting it lengthwise, and the lenses include only one thickening, wherein at all stages the tubular envelopes, made of a same material as the capillaries, or a material having substantially the same thermal extension coefficient, are used and the processes of the tubular envelopes drawing with the stocks, filling the envelopes, occurs while the pressure of the gaseous medium in the space between them is less than the pressure inside the channels of the stocks, at a temperature of the material that softens and splices the neighboring stocks, wherein each stage of the stocks producing is ended with etching the tubular envelopes of the stocks.

10. A method according to or claim 9 wherein at the process of a thickening forming a drawing speed is regulated to obtain a desired form of a cross-section of lenses.

11. A method according to claim 9, wherein for producing full lenses, cut-off of the product drawn from the furnace occurs on each side of a maximum cross-section of a thickening at distance from it that is less than a distance to a point of a knee of a thickening's generatrix.

12. A method according to claim 9, wherein for producing half-lenses, a cut-off of the product drawn from the furnace occurs on each side of a maximum cross-section of a thickening at a distance from it that is less than a distance to a point of a knee of a thickening's generatrix.

* * * * *